(12) United States Patent
Sanders et al.

(10) Patent No.: US 10,377,680 B2
(45) Date of Patent: Aug. 13, 2019

(54) POLYANIONIC POLYMERS

(71) Applicant: Verdesian Life Sciences, LLC, Cary, NC (US)

(72) Inventors: John Larry Sanders, Leawood, KS (US); Jacob Mazo, Wilmette, IL (US); Grigory Mazo, Wilmette, IL (US)

(73) Assignee: Verdesian Life Sciences, LLC, Cary, NC (US)

( * ) Notice: Subject to any disclaimer, the term of this patent is extended or adjusted under 35 U.S.C. 154(b) by 0 days.

(21) Appl. No.: 15/056,879

(22) Filed: Feb. 29, 2016

(65) Prior Publication Data

US 2016/0177004 A1   Jun. 23, 2016

Related U.S. Application Data

(63) Continuation of application No. PCT/US2014/052987, filed on Aug. 27, 2014.

(60) Provisional application No. 62/001,110, filed on May 21, 2014, provisional application No. 61/978,011, filed on Apr. 10, 2014, provisional application No. 61/870,472, filed on Aug. 27, 2013.

(51) Int. Cl.

| | |
|---|---|
| *C08F 228/02* | (2006.01) |
| *C08F 222/06* | (2006.01) |
| *C05G 3/08* | (2006.01) |
| *C08F 222/02* | (2006.01) |
| *C05G 3/00* | (2006.01) |
| *A01C 21/00* | (2006.01) |
| *A01N 25/10* | (2006.01) |
| *A01N 57/12* | (2006.01) |
| *A01N 25/34* | (2006.01) |
| *A61L 9/01* | (2006.01) |
| *A01K 1/00* | (2006.01) |
| *A01K 1/015* | (2006.01) |
| *A01N 25/30* | (2006.01) |
| *A01N 25/00* | (2006.01) |
| *C05B 7/00* | (2006.01) |
| *C05C 1/02* | (2006.01) |
| *C05C 9/00* | (2006.01) |
| *C05D 1/00* | (2006.01) |
| *C08F 218/14* | (2006.01) |
| *C08F 218/16* | (2006.01) |
| *C08F 28/02* | (2006.01) |
| *C08F 22/06* | (2006.01) |
| *A01C 1/06* | (2006.01) |

(52) U.S. Cl.
CPC .............. *C05G 3/08* (2013.01); *A01C 21/00* (2013.01); *A01K 1/0047* (2013.01); *A01K 1/0152* (2013.01); *A01N 25/00* (2013.01); *A01N 25/10* (2013.01); *A01N 25/30* (2013.01); *A01N 25/34* (2013.01); *A01N 57/12* (2013.01); *A61L 9/01* (2013.01); *C05B 7/00* (2013.01); *C05C 1/02* (2013.01); *C05C 9/00* (2013.01); *C05D 1/005* (2013.01); *C05G 3/0029* (2013.01); *C05G 3/0064* (2013.01); *C05G 3/0076* (2013.01); *C08F 222/02* (2013.01); *C08F 222/06* (2013.01); *C08F 228/02* (2013.01); *A01C 1/06* (2013.01); *C08F 22/06* (2013.01); *C08F 28/02* (2013.01); *C08F 218/14* (2013.01); *C08F 218/16* (2013.01); *Y02A 40/294* (2018.01)

(58) Field of Classification Search
CPC .... C08F 228/02; C08F 222/06; C08F 218/14; C08F 218/16; C08F 22/26; C08F 22/02; C08F 222/24; C08F 2222/245; C08F 220/38; C08F 2220/382; C05G 3/08; C05G 3/0029; A01C 21/00; A01N 25/10; A01N 25/00
See application file for complete search history.

(56) References Cited

U.S. PATENT DOCUMENTS

| | | | |
|---|---|---|---|
| 2,618,547 A | 1/1950 | Davenport et al. |
| 2,616,849 A | 11/1952 | Giammaria |
| 2,616,853 A | 11/1952 | Giammaria |
| 2,625,471 A | 1/1953 | Mowry et al. |
| 2,625,529 A | 1/1953 | Hedrick et al. |
| 2,976,138 A | 3/1961 | Hester |
| 3,052,648 A | 9/1962 | Bauer |
| 3,087,893 A | 4/1963 | Agius et al. |
| 3,130,033 A | 4/1964 | Stephens |
| 3,222,282 A | 12/1965 | Berkowitz et al. |
| 3,262,919 A | 7/1966 | Bolgiono |
| 3,308,067 A | 3/1967 | Diehl |

(Continued)

FOREIGN PATENT DOCUMENTS

| | | |
|---|---|---|
| CN | 1044025 A | 7/1990 |
| CN | 1149239 A | 5/1997 |

(Continued)

OTHER PUBLICATIONS

AVAIL MSDS dated Jan. 16, 2012.

(Continued)

*Primary Examiner* — Ling Siu Choi
*Assistant Examiner* — David L Miller
(74) *Attorney, Agent, or Firm* — Katten Muchin Rosenman LLP

(57) ABSTRACT

Novel polyanionic polymers including families of repeat units, such as maleic, itaconic, and sulfonate repeat units. The polymers are at least tetrapolymers and may be in the acid form or as partial or complete salts. The polymers may be synthesized using free radical initiators in the presence of vanadium compounds. The polymers have a variety of uses, particularly in agricultural contexts.

8 Claims, No Drawings

(56) References Cited

U.S. PATENT DOCUMENTS

| | | |
|---|---|---|
| 3,497,334 A | 2/1970 | Gee et al. |
| 3,634,052 A | 1/1972 | Gee et al. |
| 3,639,242 A | 2/1972 | Le Suer |
| 3,685,998 A | 8/1972 | Miller |
| 3,720,765 A | 3/1973 | Miller |
| 3,796,559 A | 3/1974 | Windgassen |
| 3,873,487 A | 3/1975 | Minato et al. |
| 3,936,427 A | 2/1976 | Viout et al. |
| 3,953,191 A | 4/1976 | Barton |
| 3,996,134 A | 12/1976 | Osborn et al. |
| 3,997,319 A | 12/1976 | Ott |
| 4,007,029 A | 2/1977 | Kenton |
| 4,010,006 A | 3/1977 | Price |
| 4,071,400 A | 1/1978 | Jankowiak |
| 4,076,663 A | 2/1978 | Masuda et al. |
| 4,082,533 A | 4/1978 | Wittenbrook et al. |
| 4,083,835 A | 4/1978 | Pohlemann et al. |
| 4,135,887 A | 1/1979 | Rossi |
| 4,161,539 A | 7/1979 | Stallcup |
| 4,165,743 A | 8/1979 | Denning |
| 4,173,669 A | 11/1979 | Ashida et al. |
| 4,211,765 A | 7/1980 | Johnson et al. |
| 4,251,255 A | 2/1981 | Wagner et al. |
| 4,434,231 A | 2/1984 | Jung |
| 4,439,488 A | 3/1984 | Trimnell et al. |
| 4,451,628 A | 5/1984 | Dammann |
| 4,471,100 A | 9/1984 | Tsubakimoto et al. |
| 4,538,532 A | 9/1985 | Coker |
| 4,652,273 A | 3/1987 | Maldonado et al. |
| 4,663,408 A | 5/1987 | Schulz et al. |
| 4,701,204 A | 10/1987 | Duvdevani et al. |
| 4,709,091 A | 11/1987 | Fukumoto et al. |
| 4,725,655 A | 2/1988 | Denzinger et al. |
| 4,808,215 A | 2/1989 | Gill et al. |
| 4,844,725 A | 7/1989 | Malouf et al. |
| 4,872,412 A | 10/1989 | Zollinger |
| 4,897,220 A | 1/1990 | Trieselt et al. |
| 4,923,500 A | 5/1990 | Sylling |
| 4,929,690 A | 5/1990 | Goertz et al. |
| 4,933,098 A | 6/1990 | Gutierrez et al. |
| 4,936,897 A | 6/1990 | Pipko et al. |
| 4,952,415 A | 8/1990 | Winowiski et al. |
| 5,013,769 A | 5/1991 | Murray et al. |
| 5,024,676 A | 6/1991 | Moriyama et al. |
| 5,035,821 A | 7/1991 | Chung et al. |
| 5,047,078 A | 9/1991 | Gill |
| 5,054,434 A | 10/1991 | Wax et al. |
| 5,064,563 A | 11/1991 | Yamaguchi et al. |
| 5,106,648 A | 4/1992 | Williams |
| 5,113,619 A | 5/1992 | Leps et al. |
| 5,135,677 A | 8/1992 | Yamaguchi et al. |
| 5,188,654 A | 2/1993 | Manalastas et al. |
| 5,194,263 A | 3/1993 | Chamberlain et al. |
| 5,210,163 A | 5/1993 | Grey |
| 5,223,592 A | 6/1993 | Hughes et al. |
| 5,256,181 A | 10/1993 | Manalastas et al. |
| 5,294,651 A | 3/1994 | Stephens |
| 5,300,127 A | 4/1994 | Williams |
| 5,328,624 A | 7/1994 | Chung |
| 5,336,727 A | 8/1994 | Okazawa et al. |
| 5,391,632 A | 2/1995 | Krull et al. |
| 5,399,639 A | 3/1995 | Kimpton et al. |
| 5,427,785 A | 6/1995 | Ronson et al. |
| 5,435,821 A | 7/1995 | Duvdevani et al. |
| 5,536,311 A | 7/1996 | Rodrigues |
| 5,562,916 A | 10/1996 | Van Ooijen |
| 5,574,004 A | 11/1996 | Carr |
| 5,578,486 A | 11/1996 | Zhang |
| 5,597,400 A | 1/1997 | Nonomura et al. |
| 5,653,782 A | 8/1997 | Stern et al. |
| 5,666,905 A | 9/1997 | Mackin et al. |
| 5,681,678 A | 10/1997 | Nealey et al. |
| 5,688,907 A | 11/1997 | Wood et al. |
| 5,697,186 A | 12/1997 | Neyra et al. |
| 5,732,658 A | 3/1998 | Wolters et al. |
| 5,741,521 A | 4/1998 | Knight et al. |
| 5,760,150 A | 6/1998 | Bachus |
| 5,788,722 A | 8/1998 | Emert et al. |
| 5,916,029 A | 6/1999 | Smith et al. |
| 5,993,666 A | 11/1999 | Yamaguchi et al. |
| 5,994,265 A | 11/1999 | Barclay et al. |
| 5,997,602 A | 12/1999 | Aijala |
| 6,022,555 A | 2/2000 | DeLuca et al. |
| 6,057,398 A | 5/2000 | Blum |
| 6,100,221 A | 8/2000 | Poelker et al. |
| 6,100,224 A | 8/2000 | Peiffer et al. |
| 6,139,596 A | 10/2000 | Barth et al. |
| 6,180,589 B1 | 1/2001 | Rodrigues et al. |
| 6,187,074 B1 | 2/2001 | von Locquenghien et al. |
| 6,199,318 B1 | 3/2001 | Stewart et al. |
| 6,207,780 B1 | 3/2001 | Stockhausen et al. |
| 6,210,459 B1 | 4/2001 | Sanders |
| 6,221,956 B1 | 4/2001 | Chen |
| 6,228,806 B1 | 5/2001 | Mehta |
| 6,271,191 B1 | 8/2001 | Kerobo et al. |
| 6,287,359 B1 | 9/2001 | Erhardt et al. |
| 6,309,439 B1 | 10/2001 | von Locquenghien et al. |
| 6,312,493 B1 | 11/2001 | Eltink et al. |
| 6,384,166 B1 | 5/2002 | Austin et al. |
| 6,395,051 B1 | 5/2002 | Arnold et al. |
| 6,413,292 B1 | 7/2002 | von Locquengh et al. |
| 6,444,771 B1 | 9/2002 | Yamaguchi et al. |
| 6,471,741 B1 | 10/2002 | Reinbergen |
| 6,488,734 B1 | 12/2002 | Barth et al. |
| 6,500,223 B1 | 12/2002 | Sakai et al. |
| 6,515,090 B1 | 2/2003 | Sanders et al. |
| 6,515,091 B2 | 2/2003 | Sanders et al. |
| 6,544,313 B2 | 4/2003 | Peacock et al. |
| 6,569,976 B2 | 5/2003 | Baxter et al. |
| 6,586,560 B1 | 7/2003 | Chen et al. |
| 6,632,262 B2 | 10/2003 | Gabrielson |
| 6,635,702 B1 | 10/2003 | Schmucker-Castner et al. |
| 6,653,428 B1 | 11/2003 | Klein et al. |
| 6,686,414 B1 | 2/2004 | Anderson et al. |
| 6,703,469 B2 | 3/2004 | Sanders et al. |
| 6,734,148 B2 | 5/2004 | Bell et al. |
| 6,770,616 B1 | 8/2004 | McGowan et al. |
| 6,843,846 B2 | 1/2005 | Chatterji et al. |
| 6,844,293 B2 | 1/2005 | Kirby et al. |
| 6,855,182 B2 | 2/2005 | Sears |
| 6,897,184 B2 | 5/2005 | Kurita et al. |
| 6,897,253 B2 | 5/2005 | Schmucker-Castner et al. |
| 6,930,139 B2 | 8/2005 | Sanders et al. |
| 6,936,598 B2 | 8/2005 | Khoo et al. |
| 7,004,991 B2 | 2/2006 | Narayanan et al. |
| 7,019,046 B2 | 3/2006 | Narayanan et al. |
| 7,071,259 B2 | 7/2006 | Botros |
| 7,071,275 B2 | 7/2006 | Rath et al. |
| 7,201,959 B2 | 4/2007 | Judek et al. |
| 7,217,752 B2 | 5/2007 | Schmucker-Castner et al. |
| 7,317,062 B2 | 1/2008 | Pritschins et al. |
| 7,470,304 B2 | 12/2008 | Keenan et al. |
| 7,537,705 B2 | 5/2009 | Mizuno et al. |
| 7,572,328 B2 | 8/2009 | Lettkeman et al. |
| 7,615,521 B2 | 11/2009 | Eveland et al. |
| 7,655,597 B1 | 2/2010 | Sanders |
| 7,666,241 B2 | 2/2010 | Sanders et al. |
| 7,686,863 B1 | 3/2010 | Sanders |
| 7,695,541 B1 | 4/2010 | Frizzell et al. |
| 7,923,479 B2 | 4/2011 | Champ et al. |
| 7,942,941 B2 | 5/2011 | Cravey et al. |
| 8,025,709 B2 | 9/2011 | Sanders et al. |
| 8,043,995 B2 | 10/2011 | Sanders et al. |
| 8,097,076 B2 | 1/2012 | Göbelt et al. |
| 8,110,017 B2 | 2/2012 | Wells |
| 8,143,333 B2 | 3/2012 | Peppmoller et al. |
| 8,163,859 B2 | 4/2012 | Jeon et al. |
| 8,182,593 B2 | 5/2012 | Rapp |
| 8,192,520 B2 | 6/2012 | Sanders |
| 8,420,758 B2 | 4/2013 | Durant et al. |
| 8,430,943 B2 | 4/2013 | Sanders |
| 8,436,072 B2 | 5/2013 | Herth et al. |
| 8,491,693 B2 | 7/2013 | Burnham |
| 8,562,710 B2 | 10/2013 | Palmer et al. |

(56) References Cited

U.S. PATENT DOCUMENTS

| | | |
|---|---|---|
| 8,592,343 B2 | 11/2013 | Xavier et al. |
| 8,647,406 B2 | 2/2014 | Sanders |
| 8,846,817 B2 | 9/2014 | Yontz et al. |
| 9,139,481 B2 | 9/2015 | Sanders |
| 9,145,340 B2 | 9/2015 | Sanders |
| 9,359,264 B2 | 6/2016 | Sanders |
| 9,738,565 B2 | 8/2017 | Sanders |
| 9,961,922 B2 | 5/2018 | Sanders |
| 2001/0002390 A1 | 5/2001 | Rodrigues |
| 2001/0029762 A1 | 10/2001 | Steele et al. |
| 2002/0010296 A1 | 1/2002 | Baxter et al. |
| 2002/0049139 A1 | 4/2002 | Smale |
| 2002/0098982 A1 | 7/2002 | Burnham |
| 2002/0132886 A1 | 9/2002 | Meffert et al. |
| 2002/0132949 A1 | 9/2002 | Sanders |
| 2003/0203825 A1 | 10/2003 | Aubay |
| 2003/0225233 A1 | 12/2003 | Dilocker et al. |
| 2004/0023031 A1 | 2/2004 | Sanders |
| 2004/0202634 A1 | 10/2004 | L'Alloret |
| 2004/0211234 A1 | 10/2004 | Volgas et al. |
| 2004/0226329 A1 | 11/2004 | Sanders et al. |
| 2004/0226330 A1 | 11/2004 | Sanders et al. |
| 2004/0226331 A1 | 11/2004 | Sanders et al. |
| 2004/0230020 A1 | 11/2004 | Sanders et al. |
| 2004/0265266 A1 | 12/2004 | Champ et al. |
| 2004/0266621 A1 | 12/2004 | West |
| 2005/0050931 A1 | 3/2005 | Sanders et al. |
| 2005/0090402 A1 | 4/2005 | Dieing et al. |
| 2005/0115290 A1 | 6/2005 | Sanders |
| 2005/0158268 A1 | 7/2005 | Schmucker-Castner et al. |
| 2006/0030486 A1 | 2/2006 | Meyer et al. |
| 2006/0069004 A1 | 3/2006 | Song et al. |
| 2006/0078526 A1 | 4/2006 | Boyd et al. |
| 2006/0147623 A1 | 7/2006 | Sanders |
| 2006/0191851 A1 | 8/2006 | Mizuno et al. |
| 2006/0234901 A1 | 10/2006 | Scheuing et al. |
| 2007/0027281 A1 | 2/2007 | Michl et al. |
| 2007/0161524 A1 | 7/2007 | Counradi et al. |
| 2007/0212320 A1 | 9/2007 | Demitz et al. |
| 2007/0213243 A1 | 9/2007 | Yao et al. |
| 2007/0218168 A1 | 9/2007 | Hale, III |
| 2008/0044548 A1 | 2/2008 | Hale, III |
| 2008/0173053 A1 | 7/2008 | Sanders |
| 2008/0189085 A1 | 8/2008 | Cook et al. |
| 2008/0248954 A1 | 10/2008 | Sanders |
| 2009/0071213 A1 | 3/2009 | Keenan et al. |
| 2009/0149364 A1 | 6/2009 | Beck |
| 2009/0151755 A1 | 6/2009 | Beck |
| 2009/0163365 A1 | 6/2009 | Bentlage et al. |
| 2009/0227451 A1 | 9/2009 | Rose et al. |
| 2009/0258786 A1 | 10/2009 | Pursell et al. |
| 2009/0270257 A1 | 10/2009 | Pursell et al. |
| 2009/0308122 A1 | 12/2009 | Shah |
| 2010/0012040 A1 | 1/2010 | Pow et al. |
| 2010/0024500 A1 | 2/2010 | Tyler |
| 2010/0099566 A1 | 4/2010 | Bobnock |
| 2010/0120617 A1 | 5/2010 | Dyllick-Brenzinger et al. |
| 2010/0122379 A1 | 5/2010 | Dieckmann et al. |
| 2010/0167975 A1 | 7/2010 | Vandermeulen et al. |
| 2010/0175443 A1 | 7/2010 | Sanders et al. |
| 2010/0203228 A1 | 8/2010 | Funaki et al. |
| 2010/0210802 A1 | 8/2010 | Creamer et al. |
| 2010/0234233 A1 | 9/2010 | Sannino et al. |
| 2010/0234506 A1 | 9/2010 | Elizalde et al. |
| 2010/0298526 A1 | 11/2010 | Tsumori et al. |
| 2011/0042318 A1 | 2/2011 | Painter et al. |
| 2011/0048087 A1 | 3/2011 | Sanders et al. |
| 2011/0095227 A1 | 4/2011 | Herth et al. |
| 2011/0146136 A1 | 6/2011 | Waterson et al. |
| 2011/0303157 A1 | 12/2011 | Laubenstein |
| 2012/0004383 A1 | 1/2012 | Laubender et al. |
| 2012/0055414 A1 | 3/2012 | Correa |
| 2012/0065071 A1 | 3/2012 | Li et al. |
| 2012/0118575 A1 | 5/2012 | Griffin |
| 2012/0129749 A1 | 5/2012 | Detering et al. |
| 2012/0129750 A1 | 5/2012 | Detering et al. |
| 2012/0220454 A1 | 8/2012 | Chen et al. |
| 2012/0277099 A1 | 11/2012 | Olson et al. |
| 2012/0277133 A1 | 11/2012 | DiBiase et al. |
| 2013/0078297 A1 | 3/2013 | Schlotterbeck et al. |
| 2013/0090240 A1 | 4/2013 | Yamaguchi et al. |
| 2013/0171737 A1 | 7/2013 | Way et al. |
| 2013/0212739 A1 | 8/2013 | Giritch et al. |
| 2013/0340333 A1 | 12/2013 | Vialatte et al. |
| 2014/0041431 A1 | 2/2014 | Sanders et al. |
| 2014/0106023 A1 | 4/2014 | Sanders |
| 2014/0106024 A1 * | 4/2014 | Sanders ............... A23K 1/1609 426/2 |
| 2014/0315716 A1 | 10/2014 | Matheny et al. |
| 2014/0342905 A1 | 11/2014 | Bullis et al. |
| 2015/0033811 A1 | 2/2015 | Sanders |
| 2016/0174547 A1 | 6/2016 | Sanders et al. |
| 2016/0174549 A1 | 6/2016 | Sanders et al. |
| 2016/0175469 A1 | 6/2016 | Sanders et al. |
| 2016/0177004 A1 | 6/2016 | Sanders et al. |
| 2016/0185678 A1 | 6/2016 | Sanders et al. |
| 2016/0272553 A1 | 9/2016 | Sanders et al. |

FOREIGN PATENT DOCUMENTS

| | | | |
|---|---|---|---|
| CN | 1524184 | A | 8/2004 |
| CN | 1684926 | A | 10/2005 |
| CN | 1962565 | A | 5/2007 |
| CN | 101423431 | A | 5/2009 |
| CN | 101519324 | A | 9/2009 |
| CN | 101575243 | A | 11/2009 |
| CN | 101580409 | | 11/2009 |
| CN | 101792348 | A | 8/2010 |
| CN | 101830571 | A | 9/2010 |
| CN | 101885798 | A | 11/2010 |
| CN | 101885888 | A * | 11/2010 |
| CN | 102154013 | A | 8/2011 |
| CN | 101830571 | B * | 6/2012 |
| DE | 2558551 | A1 | 7/1977 |
| DE | 2822488 | A1 | 11/1979 |
| DE | 4122490 | A1 | 1/1993 |
| DE | 4132620 | A1 | 4/1993 |
| EP | 0290807 | A2 | 11/1988 |
| EP | 0314070 | A2 | 5/1989 |
| EP | 0337694 | A2 | 10/1989 |
| EP | 0683985 | A1 | 11/1995 |
| EP | 0877076 | A2 | 11/1998 |
| EP | 0892111 | A1 | 1/1999 |
| EP | 0976699 | A1 | 2/2000 |
| EP | 1024692 | A1 | 8/2000 |
| EP | 1230195 | A1 | 8/2002 |
| EP | 2135854 | A2 | 12/2009 |
| GB | 1324087 | | 7/1973 |
| JP | 54050027 | A | 4/1979 |
| JP | 54077294 | A | 6/1979 |
| JP | S58131903 | A | 8/1983 |
| JP | 60101194 | A | 5/1985 |
| JP | 62096046 | A | 5/1986 |
| JP | 61282301 | A | 12/1986 |
| JP | S63-042636 | A | 2/1988 |
| JP | 63083169 | A | 4/1988 |
| JP | 63148937 | A | 6/1988 |
| JP | 03112426 | | 5/1991 |
| JP | H07215746 | A | 8/1995 |
| JP | 08092591 | A | 4/1996 |
| JP | H10-045504 | A | 2/1998 |
| JP | 11092788 | A | 4/1999 |
| JP | 2008023433 | A | 2/2008 |
| RU | 2051884 | C1 | 1/1996 |
| RU | 2375065 | C2 | 12/2009 |
| RU | 2378869 | C1 | 1/2010 |
| WO | 9715367 | A1 | 5/1997 |
| WO | 9918785 | A1 | 4/1999 |
| WO | 9948833 | A1 | 9/1999 |
| WO | WO 2002/071086 | A1 | 9/2002 |
| WO | WO 2003/074447 | A2 | 9/2003 |
| WO | 2006131213 | A1 | 12/2006 |
| WO | 2007003388 | A2 | 1/2007 |
| WO | 2009060012 | A2 | 5/2009 |

(56) References Cited

FOREIGN PATENT DOCUMENTS

| | | |
|---|---|---|
| WO | 2009061930 A1 | 5/2009 |
| WO | WO 2010/121976 A2 | 10/2010 |
| WO | WO 2011/043941 A2 | 4/2011 |
| WO | WO 2014/062480 A1 | 4/2014 |
| WO | 2015031521 A1 | 3/2015 |
| WO | 2015035031 A1 | 3/2015 |
| WO | 2015116716 A1 | 8/2015 |
| WO | 2015179552 A1 | 11/2015 |
| WO | 2015179687 A1 | 11/2015 |

OTHER PUBLICATIONS

Aziz, et al. *Efficiency of Slow Release Urea Fertilizer on Herb Yield and Essential Oil Production of Lemon Balm (Melissa Officinalis L.) Plant.* American-Eurasian J. Agric. & Environ. Sci., [Online] 5(2) :141-147, 2009.

Blair. Sulphur Enhanced Fertilizer (SEF). A new generation of fertilizers. The Proceedings of the International Plant Nutrition Colloquium XVI, Department of Plant Sciences, UC Davis, [Online] 2009.

Chen, et al. *Effect of a Polymer on Mitigating Ammonia Emission from Liquid Dairy Manure.* Efekat polimera na smanjenje emisije /Polj. tehn. (Jan. 2013), 1-13.

Chiba, Lee I. *Animal Nutrition Handbook, Section 12: Poultry Nutrition and Feeding.* pps. 316-331, 2009—available online at http://www.ag.auburn.edu/%7Echibale/an12poultryfeeding.pdf.

Chien et al. *Review of Maleic-Itaconic Acid Copolymer Purported as Urease Inhibitor and Phosphorus Enhancer in Soils..* Agronomy Journal 106(2) : 423-430, 2014.

CN Search Report in Application No. 201080047969.4 received with First Office Action dated Jul. 31, 2013.

Davidson et al. *Persistence of Rhizobium japonicum on the Soybean Seed Coat Under Controlled Temperature and Humidity.* Applied and Environmental Microbiology, 35 : 94-96, 1978.

EP Search Report 1 dated Jun. 16, 2016 in related Application No. 13847267.5.

EP Search Report 2 dated Jun. 10, 2016 in related Application No. 16161777.4.

EP Search Report 3 dated Jun. 13, 2016 in related Application No. 16161780.8.

EP Search Report 4 dated Jul. 26, 2016 in related Application No. 16161783.2.

EP Search Report 5 dated Jun. 13, 2016 in related Application No. 16161786.5.

EP Search Report 6 dated Jun. 20, 2016 in related Application No. 16161785.7.

Gay, et al. *Ammonia Emissions and Animal Agriculture.* Virginia Cooperative Extension, Publication 442-110, Virginia Polytechnic Institute and State University, 2009.

*Grains/Fertilizers*, article found online at martinsachs.angelfire.com/feeding.html, dated Apr. 11, 2010.

Groenstein, C.M. et al. *Measures to Reduce Ammonia Emissions from Livestock Manures; Now, Soon, Later.* Wageningen UK Livestock Research; Report 488; Jun. 2011.

Herrington et al. *Rheological modification of bitumen with maleic anhydride and dicarboxylic acids.* Fuel, 78 : 101-110, 1999.

International Preliminary Report on Patentability 1 in corresponding application PCT/US2014/052987, dated Mar. 10, 2016.

International Preliminary Report on Patentability 2 in related application PCT/US 2014/054069, dated Dec. 11, 2014.

International Search Report and Written Opinion 1 in related application PCT/US 2010/050244, dated Jun. 27, 2011.

International Search Report and Written Opinion 2 in related application PCT/US 2013/064378, dated Jan. 23, 2014 (Note: for cited reference RU2375063, see U.S. Pat. No. 6,936,598).

International Search Report and Written Opinion 3 in related application PCT/US 2013/054373, dated Dec. 12, 2013.

International Search Report and Written Opinion 4 in corresponding application PCT/US 2014/052987, dated Jan. 16, 2015.

International Search Report and Written Opinion 5 in related application PCT/US 2014/054069, dated Dec. 11, 2014.

International Search Report and Written Opinion 6 in related application PCT/US 2014/049451, dated Dec. 18, 2014.

International Search Report and Written Opinion 7 in related application PCT/US 2014/039424, dated Oct. 16, 2014.

International Search Report and Written Opinion 8 in related application PCT/US 2015/013345, dated Apr. 13, 2015.

International Search Report and Written Opinion 9 in related application PCT/US 2015/032037, dated Aug. 28, 2015.

International Search Report and Written Opinion 10 in related application PCT/US 2015/031823, dated Aug. 28, 2015.

Jung et al. *Polymer-entrapped rhizobium as an inoculants for legumes.* Plant and Soil, 65 : 219-231, 1982.

Kahraman et al. *Bioengineering Polyfunctional Copolymers. VII. Synthesis and characterization of copolymers of p-vinylphenyl boronic acid with maleic and citraconic anhydrides and their self-assembled macrobranched supramolecular architectures.* Polymer 45 :5813-5828, 2004.

Kejun et al., *Copolymerization of cis-Butenedioic Acid with Sodium Methallylsulfonate in Aqueous Solution.* J. App. Poly. Sci., vol. 40 : 1529-1539; 1990.

Li et al. *Dispersion and Rheological Properties of Concentrated Kaolin Suspensions with Polycarboxylate Copolymers Bering Comb-like Side Chains.* Journal of the European Ceramic Society, 34(1) :137-146, Jan. 2014.

Machida et al. *Water Soluble Polymers. Ix. N-(2-chloroethyl)-sulfonamides of Styrene-maleic Acid and Styrene-itaconic Acid Copolymers.* Sen'i Gakkaishi 22(6) :269-73,1996.

Mohan, Prasanthrajan et al. *Addressing the Challenges of Ammonia Loss from Poultry Droppings through Indigenous Carbon Wastes.* International Journal of Environmental Science and Development, 3 (4), Aug. 2012—available online at http://www.ijesd.org/papers/255-D590.pdf.

Naga et al. *Polymeric Additives for Pour Point Depression of Residual Fuel Oils.* J. Chem. Tech. Biotechnol. 35A : 241-247, 1985.

Patterson, Paul H. *Hen House Ammonia: Environmental Consequences and Dietary Strategies.* Multi-State Poultry Meeting, May 14-16, 2002—available online at http://www.ijesd.org/papers/255-D590.pdf.

Powers, Wendy. Practices to Reduce Ammonia. 2004—available online at http://www.thepoultrysite.com/articles/219/practices-to-reduce-ammonia.

Prochnow, L.I. et al. *Controlling Ammonia Losses During Manure Composting with the Addition of Phosphogypsum and Simple Superphosphate.* Sci.Agri., Piracicaba, 52(2) :346-349, mai/ago 1995.

Puoci et al. *Polymer in Agriculture: a Review.* American Journal of Agricultural and Biological Sciences, 3 :299-314, 2008.

Sanderson, et al. *Effect of Gypsum and Elemental Sulphur on Calcium and Sulphur Content of Rutabagas in Podzolic Soils.* Can J Plan Sci [Online], pp. 785-788, 2002.

Shakkthivel et al. *Newly Developed Itaconic Acid Copolymers for Gypsum and Calcium Carbonate Scale Control.* Journal of Applied Polymer Science, 103(5) :3206-3213, 2007.

Singh, A. et al. *Efficacy of Urease Inhibitor to Reduce Ammonia Emission from Poultry Houses.* J. Appl. Poult. Res., 18 :34-42, 2009—available online at http://japr.fass.org/content/18/1/34.full.

*Sodium Lignosulphonate.* Available online at www.xyd-chem.com on Apr. 20, 2010.

US Provisional Patent Application entitled Polyanionic Polymers, U.S. Appl. No. 62/001,110, filed May 21, 2014.

Weir, B.S. The current taxonomy of rhizobia. NZ Rhizobia website. http://www.rhizobia.co.nz/taxonomy/rhizobia; Partial update: May 2, 2013.

Yang, Charles Q. et al. *In-situ Polymerization of Maleic Acid and Itaconic Acid and Crosslinking of Cotton Fabric.* Textile Research Journal, 69(10) :782-789, 1999.

Yang, Charles Q. et al. *In-situ Polymerization of Maleic Acid and Itaconic Acid on Cotton: MALDI/TOF Mass Spectroscopy and Light-Scattering Study.* Textile Research Journal, 70(4) :359-62, 2000.

(56) References Cited

OTHER PUBLICATIONS

Yasmin, et al. *Effect of Elemental Sulfur, Gypsum, and Elemental Sulfur Coated Fertilizers on the Availability of Sulfur to Rice*. J Plant Nutr [Online], 20(1): 79-91, 2007.
Zhang et al. *Synthesis and Inhibition Efficiency of a Novel Quadripolymer Inhibitor*. Chin. J. Ch. E. 15(4) :600; 2007.
The definition of "including", Merriam-Webster Online Dictionary, [Retrieved from the Internet Oct. 1, 2016: <URL: http://www.merriam-webster.com/dictionary/include>].
U.S. Appl. No. 15/056,886, Non-Final Office Action dated Jan. 26, 2017.
U.S. Appl. No. 15/056,892, Non-Final Office Action dated Oct. 13, 2016.
U.S. Appl. No. 15/056,892, Final Office Action dated May 19, 2017.
Supplemental/Extended Search Report for EP application 14841015.2 dated Mar. 30, 2017.
U.S. Appl. No. 14/915,072, Non-Final Office Action dated Aug. 4, 2017.
U.S. Appl. No. 15/056,886, Non-Final Office Action dated Sep. 14, 2017.
U.S. Appl. No. 15/056,892, Notice of Allowance dated Sep. 20, 2017.
Blaylock, A., et al., "Optimizing N Management Without Ammonium Nitrate,"Fluid Journal, 14(2): 20-22 (2006).
Goos, R.J., "A Comparison of a Maleic-Itaconic Polymer and N-(n-butyl) Thiophosphoric Triamide as Urease Inhibitors," Soil Science Society of America Journal, 77(4): 1418-1423 (Jun. 4, 2013).
U.S. Appl. No. 15/056,889, Non-Final Office Action dated Jun. 29, 2018.
U.S. Appl. No. 14/915,072, Notice of Allowance dated Aug. 16, 2018.
U.S. Appl. No. 15/056,892, Notice of Allowance dated Apr. 11, 2018.
U.S. Appl. No. 15/056,886, Notice of Allowance dated Apr. 24, 2018.
Notification for Reasons of Refusal in co-pending Japenese Application No. 2016-537823 dated May 15, 2018.
Communication pursuant to Article 94(3) EPC issued in connection with EP application 16161786.5 dated Mar. 13, 2018.
Communication pursuant to Article 94(3) EPC issued in connection with EP application 16161780.8 dated Feb. 9, 2018.
Non-Final Office Action in U.S. Appl. No. 14/915,072 dated Mar. 21, 2018.
Communication pursuant to Article 94(3) EPC issued in connection with EP application 16161785.7 dated Feb. 19, 2018.

\* cited by examiner

POLYANIONIC POLYMERS

CROSS-REFERENCE TO RELATED APPLICATIONS

This is a continuation of International Application No. PCT No. PCT/US2014/052987, filed Aug. 27, 2014, claiming the benefit of three (3) U.S. provisional applications: Ser. No. 61/870,472, filed Aug. 27, 2013, Ser. No. 61/978,011, filed Apr. 10, 2014; and Ser. No. 62/001,110, filed May 21, 2014. The PCT and provisional applications are all incorporated herein by reference in their entireties.

BACKGROUND OF THE INVENTION

Field of the Invention

The present invention is broadly concerned with a new class of substantially water soluble, biodegradable polyanionic polymers and syntheses thereof finding particular utility in agricultural uses, e.g., directly applied to soil, or in combination with fertilizers to increase nutrient uptake; as seed coatings and pesticide adjuvants; to reduce atmospheric ammonia derived from animal manures; as animal feed and water amendments; and to inhibit nitrification, urease hydrolysis, and phosphate fixation in soils. More particularly, the invention is concerned with novel polymers that are at least tetrapolymers and preferably contain specific types of carboxylic and sulfonate repeat units, as well as methods of synthesizing dicarboxylate/sulfonate polymers including the novel polymers hereof. Other uses of the polyanionic polymers are also disclosed, alone or in combination with other polyanionic (e.g., dicarboxylic) polymers and/or other functional ingredients.

Description of the Prior Art

For a number of years, Specialty Fertilizer Products, LLC of Leawood, Kans., has commercialized a series of aqueous dispersions of maleic-itaconic polymers in partial salt form. These products include AVAIL® for use with granular and liquid fertilizers (respectively the partial sodium and ammonium salts), and NUTRISPHERE-N® for use with granular and liquid fertilizers (the partial calcium salt). For example, such products may be sprayed or otherwise applied to the surface of solid fertilizers, such as urea, ammonium salts, monoammonium phosphate (MAP), diammonium phosphate (DAP), potash, and gypsum, or mixed with liquid fertilizers, such as UAN and ammonium polyphosphate.

These prior products have been shown to have a number of outstanding agricultural properties, including the ability to enhance the uptake of fertilizer nutrients (e.g., phosphates, nitrogen, potassium, and micronutrients), to act as adjuvants for pesticides such as glyphosate herbicides, and, when supplemented with an organic drying agent, to very quickly dry when applied to solid fertilizers, thereby facilitating production of final coated solid fertilizer products. Moreover, the preferred polymers have been shown to have enhanced activity when fertilizer formulations containing different types of polymer partial salts are employed (U.S. Patent Publication No. 2009-0217723). This technology is also described in U.S. Pat. Nos. 6,515,090, 7,655,597, 7,736,412, and 8,043,995, and related patents.

Notwithstanding the success of the prior maleic-itaconic polymers, agriculturally useful polymers having even greater activities would be desirable.

SUMMARY OF THE INVENTION

The present invention overcomes the problems outlined above and provides a new class of polymers preferably having a high carboxylate content and sulfonate repeat units, which are very soluble in water and biodegradable. As used herein, "polymer" is a broad term, which embraces homopolymers and copolymers, the latter containing any number of different repeat units or moieties, such as terpolymers or tetrapolymers. The preferred novel polymers hereof are at least tetrapolymers having at least four different repeat units distributed along the lengths of the polymer chains, preferably with at least one repeat unit each of maleic, itaconic, and sulfonate repeat units. The repeat units are advantageously derived from corresponding monomers used in the synthesis of the polymers, and have at least one repeat unit from each of three separately defined categories of repeat units, referred to herein as type B, type C, and type G repeat units, and explained in detail below.

The invention has a number of aspects, relating to the new polymers, synthesis of polyanionic polymers, and various uses of the new polymers, alone or in conjunction with other anionic polymers.

1. The New Polymers

The new anionic polymers comprise at least four repeat units distributed along the length of the polymer chain, the at least four repeat units including at least one each of type B, type C, and type G repeat units, the type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat units may be substituted with one or more C1-C6 straight or branched chain alkyl groups substantially free of ring structures and halo atoms, and wherein the salts have salt-forming cations selected from the group consisting of metals, amines, and mixtures thereof, the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more C1-C6 straight or branched chain alkyl groups substantially free of ring structures and halo atoms, and wherein the salts have salt-forming cations selected from the group consisting of metals, amines, and mixtures thereof, the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more C1-C6 straight or branched chain alkyl groups substantially free of ring structures and halo atoms, and wherein the salts of the type G repeat units have salt-forming cations selected from the group consisting of metals, amines, and mixtures thereof, at least about 90 mole percent of the repeat units therein are selected from the group consisting of type B, C, and G repeat units, and mixtures thereof, the repeat units being randomly located along the polymer, the polymer containing no more than about 10 mole percent of any of (I) non-carboxylate olefin repeat units, (ii) ether repeat units, and (iii) non-sulfonated monocarboxylic repeat units.

Preferably, the polymers comprise at least about 96 mole percent of the repeat units therein selected from the group consisting of type B, C, and G repeat units, and mixtures thereof, and still more preferably consist essentially of repeat units selected from the group consisting of type B, C, and G repeat units, and mixtures thereof. The polymers are also substantially free of ester groups and noncarboxylate olefin groups.

Especially preferred polymers have one type B repeat unit, one type C repeat unit, and two different type G repeat units, especially where the one type B repeat unit is derived from maleic acid, the one type C repeat unit is derived from itaconic acid, and two type G repeat units are respectively derived from methallylsulfonic acid and allylsulfonic acid. In such polymers, the type B repeat unit is present at a level of from about 35-55 mole percent, the type C repeat unit is present at a level of from about 20-55 mole percent, the type G repeat unit derived from methallylsulfonic acid is present at a level of from about 1-25 mole percent, and the type G repeat unit derived from allylsulfonic acid is present at a level of from about 1-25 mole percent, where the total amount of all of the repeat units in the polymer is taken as 100 mole percent. Other useful polymers comprise two different type B repeat units, one type C repeat unit, and one type G repeat unit, and where the polymer has at least one repeat unit not selected from the group consisting of type B, type C, and type G repeat units.

Advantageously, the total amount of type B repeat units in the polymer is from about 1-70 mole percent, the total amount of type C repeat units in the polymer is from about 1-80 mole percent, and the total amount of type G repeat units in the polymer is from about 0.1-65 mole percent, where the total amount of all of the repeat units in the polymer is taken as 100 mole percent. Still more preferably, the total amount of type B repeat units in the polymer is from about 20-65 mole percent, the total amount of type C repeat units in the polymer is from about 15-75 mole percent, and the total amount of type G repeat units in the polymer is from about 1-35 mole percent, where the total amount of all of the repeat units in the polymer is taken as 100 mole percent.

The novel polymers generally have a molecular weight of from about 800-50,000, and more preferably from about 1000-5000. The polymers of the invention may be in a free acid form or in partial or complete salt form, including one or more salt-forming cations bound with the polymer. Such salt-forming cations are usually selected from the group consisting of cations of metals, amines, micronutrients, and mixtures thereof, and especially those selected from the group consisting of alkali, alkaline earth, and transition metal cations.

The polymers of the invention may be used alone or in combination with another anionic polymer including maleic and itaconic repeat units. Moreover, polymer-containing formulations may be prepared comprising a polymer in accordance with the invention in combination with one or more other ingredients, selected from the group consisting of boric acid, boron-containing compounds, boric compound solvents, alcohols, diols, polyols, organic acids, polyvinyl alcohols, dyes, and mixtures thereof.

2. Polymer Synthesis

The invention also provides polymer synthesis methods useful for the production of a variety of polymers containing dicarboxylate and sulfonate repeat units, including the novel polymers of the invention. Such methods comprise the steps of:

forming an aqueous dispersion containing dicarboxylate and sulfonate repeat unit monomers, the dicarboxylate repeat unit monomers selected from the group consisting of type B repeat unit monomers, type C repeat unit monomers, and mixtures thereof, the type B repeat unit monomers selected from the group consisting of substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat unit monomers may be substituted with one or more C1-C6 straight or branched chain alkyl groups substantially free of ring structures and halo atoms, and wherein the salts have salt-forming cations selected from the group consisting of metals, amines, and mixtures thereof, the type C repeat unit monomers selected from the group consisting of substituted or unsubstituted monomers of itaconic acid, itaconic anhydride, and any isomers, esters, and the partial or complete salts of any of the foregoing, and mixtures of any of the foregoing, wherein the type C repeat unit monomers may be substituted with one or more C1-C6 straight or branched chain alkyl groups substantially free of ring structures and halo atoms, and wherein the salts have salt-forming cations selected from the group consisting of metals, amines, and mixtures thereof, the sulfonate repeat unit monomers selected from the group consisting of type G repeat unit monomers, the type G repeat unit monomers selected from the group consisting of substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat unit monomers may be substituted with one or more C1-C6 straight or branched chain alkyl groups substantially free of ring structures and halo atoms, and wherein the salts of the type G repeat unit monomers have salt-forming cations selected from the group consisting of metals, amines, and mixtures thereof;

heating the dispersion to an elevated temperature of from about 50-125° C. and adding a vanadium compound to the dispersion; and thereafter adding a free radical initiator comprising at least about 95% by weight hydrogen peroxide to the dispersion, and causing the monomers within the dispersion to polymerize in an oxygen-containing environment until at least about 90% by weight of the monomers have been converted to the polymer.

In preferred forms, the vanadium compound is added to the dispersion after the heating step, and the free radical initiator is added over a period of from about 30 minutes-24 hours while maintaining the dispersion at the elevated temperature. The free radical initiator also preferably consists essentially of hydrogen peroxide. The synthesis is best carried out with the exclusion of substantial amounts of dissolved iron species and sulfate salts, and in an ambient air environment. The polymerization is usually carried out until at least about 98% by weight of the monomers have been converted to the polymer.

In preferred forms, the monomers comprise maleic monomers, itaconic monomers, allylsulfonate monomers, and methallylsulfonate monomers, and the vanadium compound is vanadium oxysulfate. The polymers may be recovered in the acid form or be converted to partial or complete salts.

For best results, the type B repeat units are present at a level of less than 50 mole percent, and the repeat units are randomly dispersed throughout the polymer.

In another aspect of the synthesis method, a polymer containing dicarboxylate and sulfonate repeat units may be prepared by a method comprising the steps of:
- forming an aqueous dispersion containing dicarboxylate and sulfonate monomers;
- heating the dispersion to an elevated temperature of from about 50-125° C. and adding a vanadium compound to the dispersion; and
- thereafter adding a free radical initiator comprising at least about 95% by weight hydrogen peroxide to the dispersion, and causing the monomers within the dispersion to polymerize in an oxygen-containing environment until at least about 90% by weight of the monomers have been converted to the polymer.

In preferred forms of this method, the vanadium compound is added to the dispersion after the heating step, and the free radical initiator is added over a period of from about 30 minutes-24 hours while maintaining the dispersion at the elevated temperature. The free radical initiator preferably consists essentially of hydrogen peroxide, and the dispersion is prepared with the exclusion of substantial amounts of dissolved iron species and sulfate salts.

The polymerization is best carried out in an ambient air environments, and until at least about 98% by weight of the monomers have been converted to the polymer. The monomers comprise maleic monomers, itaconic monomers, allylsulfonate monomers, and methallylsulfonate monomers, and the vanadium compound is vanadium oxysulfate. As before, the polymers may be recovered in the acid form or as partial or complete salts.

3. Fertilizer Products

The invention also provides agricultural products and uses thereof, wherein the products comprise fertilizer and a polymer mixed with the fertilizer, the polymer being an anionic polymer comprising at least four repeat units distributed along the length of the polymer chain, the at least four repeat units including at least one each of type B, type C, and type G repeat units, the type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat units may be substituted with one or more C1-C6 straight or branched chain alkyl groups substantially free of ring structures and halo atoms, and wherein the salts have salt-forming cations selected from the group consisting of metals, amines, and mixtures thereof, the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more C1-C6 straight or branched chain alkyl groups substantially free of ring structures and halo atoms, and wherein the salts have salt-forming cations selected from the group consisting of metals, amines, and mixtures thereof, the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more C1-C6 straight or branched chain alkyl groups substantially free of ring structures and halo atoms, and wherein the salts of the type G repeat units have salt-forming cations selected from the group consisting of metals, amines, and mixtures thereof, the anionic polymer containing no more than about 10 mole percent of non-carboxylate olefins and/or ethers.

The fertilizer may be a solid fertilizer, and particularly granular, and the polymer is applied to the fertilizer as a liquid dispersion. Alternately, the fertilizer may be in liquid form, and the polymer is mixed with the liquid fertilizer. The fertilizers are preferably selected from the group consisting of starter fertilizers, phosphate-based fertilizers, fertilizers containing nitrogen, phosphorus, potassium, calcium, magnesium, boron, zinc, manganese, copper, or molybdenum materials. One especially preferred solid fertilizer is urea. Where the fertilizers are solid, the polymers is preferably present at a level of from about 0.001-20 g per 100 g of the fertilizer. The tetrapolymers of the invention may be used alone or in combination with another anionic polymer including maleic and itaconic repeat units.

More generally, the invention provides agricultural products comprising fertilizer and a polymer mixed with the fertilizer, the polymer being an anionic polymer comprising at least four repeat units distributed along the length of the polymer chain, and the repeat units include at least one each of a maleic, itaconic, and sulfonate repeat unit. Most preferably the polymer is a tetrapolymer and having maleic and itaconic repeat units, and two different sulfonate repeat units. The polymers may be recovered in the free acid form or as partial or complete salts, and in preferred forms include an amount of a micronutrient that is preferably bound or complexed with the polymer.

All of the fertilizer/polymer products of the invention may be used by applying such products to soil.

4. Pesticide Products

The invention provides pesticide products comprising a pesticide and a polymer, the polymer being an anionic polymer comprising at least four repeat units distributed along the length of the polymer chain, the at least four repeat units including at least one each of type B, type C, and type G repeat units, the type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat units may be substituted with one or more C1-C6 straight or branched chain alkyl groups substantially free of ring structures and halo atoms, and wherein the salts have salt-forming cations selected from the group consisting of metals, amines, and mixtures thereof, the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more C1-C6 straight or branched chain alkyl groups substantially free of ring structures and halo atoms, and wherein the salts have salt-forming cations selected from the group consisting of metals, amines, and mixtures thereof, the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more C1-C6 straight or branched chain alkyl groups substantially free of ring structures and halo atoms, and wherein the salts of the type G repeat units have salt-forming cations selected from the group consisting of metals, amines, and mixtures thereof, the anionic polymer containing no more than about 10 mole percent of non-carboxylate olefins and/or ethers.

A wide variety of pesticides may be used in these products, such as those selected from the group consisting of herbicides, insecticides, fungicides and nematocides. The complete product may be in solid, liquid or aerosol form, and may also include another polymer including maleic and itaconic repeat units. The polymers may be in acid form, or as partial or complete salts.

More generally, the invention provides pesticide products comprising a pesticide and a polymer, the polymer being an anionic polymer comprising at least four repeat units distributed along the length of the polymer chain, the repeat units including at least one each of a maleic, itaconic, and sulfonate repeat unit.

Particularly preferred compositions comprise a polymer mixed with glyphosate and micronutrients, the polymer being an anionic polymer comprising at least four repeat units distributed along the length of the polymer chain, the repeat units including at least one each of a maleic, itaconic, and sulfonate repeat unit. Again, the polymers of these compositions may be in combination with another anionic polymer including maleic and itaconic repeat units, and the micronutrients may be complexed with the polymer. The polymers may be in acid form, or as partial or complete salts.

All of the pesticide products of the invention may be used in pesticidal methods comprising the step of applying the products to soil, hard surfaces, or the leaves of plants.

5. Sulfur Products

The invention further provides products comprising a compound selected from the group consisting of gypsum, one or more members of the Kieserite Group, potassium magnesium sulfate, elemental sulfur, and mixtures thereof, and a polymer, the polymer being an anionic polymer comprising at least four repeat units distributed along the length of the polymer chain, the at least four repeat units including at least one each of type B, type C, and type G repeat units, the type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat units may be substituted with one or more C1-C6 straight or branched chain alkyl groups substantially free of ring structures and halo atoms, and wherein the salts have salt-forming cations selected from the group consisting of metals, amines, and mixtures thereof, the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more C1-C6 straight or branched chain alkyl groups substantially free of ring structures and halo atoms, and wherein the salts have salt-forming cations selected from the group consisting of metals, amines, and mixtures thereof, the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more C1-C6 straight or branched chain alkyl groups substantially free of ring structures and halo atoms, and wherein the salts of the type G repeat units have salt-forming cations selected from the group consisting of metals, amines, and mixtures thereof, the anionic polymer containing no more than about 10 mole percent of non-carboxylate olefins and/or ethers.

Preferably, the compound comprises gypsum, and the polymer is present at a level of from about 0.01-10% w/w (more preferably from about 0.05-2% w/w), where the total weight of the polymer and the compound is taken as 100% by weight. At least about 80 mole percent of the polymer repeat units contain at least one anionic group. More preferably, the polymer has from about 1-70 mole percent of the type B repeat units, from about 15-75 mole percent of the type C repeat units, and from about 0.1-65 mole percent of the type G repeat units, and the total abundance of the type B, C, and G repeat units being at least about 90 mole percent. The polymer may have a molecular weight from about 800-50,000.

More generally, the products of this aspect of the invention comprise a compound selected from the group consisting of gypsum, one or more members of the Kieserite Group, potassium magnesium sulfate, elemental sulfur, and mixtures thereof, and a polymer, the polymer being an anionic polymer comprising at least four repeat units distributed along the length of the polymer chain, the repeat units including at least one each of a maleic, itaconic, and sulfonate repeat unit.

The sulfur products of the invention are used to fertilize soil by applying the products to soil.

6. Liquid or Solutionized Fertilizer Products

In another aspect of the invention, liquid or solutionized fertilizer products (e.g., gypsum or UAN) are provided including a fertilizer in aqueous dispersion, and a polyanionic polymer comprising at least four repeat units distributed along the length of the polymer chain, the repeat units including at least one each of a maleic, itaconic, and sulfonic repeat unit, and an amount of an alpha-hydroxy acid formulation. The fertilizer product normally is an aqueous dispersion having a pH of from about 4-7, or from about 0.5-3.

Preferably, the alpha-hydroxy acids are saturated and essentially free of double bonds and carbon ring structures, and are selected from the group consisting of lactic acid, glycolic acid, citric acid, tartaric acid, tartronic acid, glyceric acid, and dihydroxypropanedioic acid, and mixtures thereof.

Overall, the fertilizer products preferably contain from about 10-45% w/w of the polymer, from about 3-60% w/w of the alpha-hydroxy acid, with the balance being solvent. The polymer advantageously has at least four repeat units distributed along the length of the polymer chain, the repeat units including at least one each of a maleic, itaconic, and sulfonate repeat unit. In particularly preferred forms, the polymer comprises at least four repeat units including at least one each of type B, type C, and type G repeat units, the type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat units may be substituted with one or more C1-C6 straight or branched chain alkyl groups substantially free of ring structures and halo atoms, and wherein the salts have salt-forming cations selected from the group consisting of metals, amines, and mixtures thereof, the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more C1-C6 straight or branched chain alkyl groups substantially free of ring structures and halo atoms, and wherein the salts have salt-forming cations selected from the group consisting of metals, amines, and mixtures thereof, the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more C1-C6 straight or branched chain alkyl groups substantially free of ring structures and halo atoms, and wherein the salts of the type G repeat units have salt-forming cations selected from the group consisting of metals, amines, and mixtures thereof, at least about 90 mole percent of the repeat units therein are selected from the group consisting of type B, C, and G repeat units, and mixtures thereof, the repeat units being randomly located along the polymer, the polymer containing no more than about 10 mole percent of any of (I) non-carboxylate olefin repeat units, (ii) ether repeat units, and (iii) non-sulfonated monocarboxylic repeat units.

The fertilizer products of the invention may also be improved by the presence of an amount of a polyvinyl alcohol (PVA) therein, especially at a level of from about 0.1-10% w/w. Moreover, a plurality of different PVAs may be employed. The PVA should have a hydrolysis level of at least about 97 mole percent. The products may also include another polymer having maleic and itaconic repeat units therein.

The liquid or solutionized products of the invention are used by applying such products to soil.

7. Potassium Products

The invention in another aspect provides potassium products comprising at least partially water soluble potassium-containing solids, e.g., potassium chloride, having thereon the dried residue of an aqueous additive comprising a polymer salt containing a plurality of anionic repeat units including maleic and itaconic repeat units, with substantially all of the salt-forming cations of the polymer salt being alkali metal cations, the aqueous additive having a pH of from about 0.1-4 (more preferably from about 0.5-3, and most preferably about 1). The polymer is preferably present on the surface of the potassium-containing solids at a level of from about 0.001-10% by weight, based upon the total weight of the product taken as 100% by weight. The aqueous additive may also contain a carboxymethyl cellulose salt.

The polymer is advantageously at least a tetrapolymer and comprises at least four repeat units distributed along the polymer chain, the repeat units including at least one each of a maleic, itaconic, and sulfonate repeat unit. More preferably, the polymer as at least one each of type B, type C, and type G repeat units, the type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat units may be substituted with one or more C1-C6 straight or branched chain alkyl groups substantially free of ring structures and halo atoms, and wherein the salts have salt-forming cations selected from the group consisting of metals, amines, and mixtures thereof, the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more C1-C6 straight or branched chain alkyl groups substantially free of ring structures and halo atoms, and wherein the salts have salt-forming cations selected from the group consisting of metals, amines, and mixtures thereof, the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more C1-C6 straight or branched chain alkyl groups substantially free of ring structures and halo atoms, and wherein the salts of the type G repeat units have salt-forming cations selected from the group consisting of metals, amines, and mixtures thereof, at least about 90 mole percent of the repeat units therein are selected from the group consisting of type B, C, and G repeat units, and mixtures thereof, the repeat units being randomly located along the polymer, the polymer containing no more than about 10 mole percent of any of (I) non-carboxylate olefin repeat units, (ii) ether repeat units, and (iii) non-sulfonated monocarboxylic repeat units.

Preferably, at least about 96 mole percent of the repeat units therein are selected from the group consisting of type B, C, and G repeat units, and mixtures thereof, and still more preferably the repeat units consist essentially of repeat units selected from the group consisting of type B, C, and G repeat units, and mixtures thereof; for best results, the polymer is substantially free of ester and noncarboxylate olefin groups.

In another aspect, the polymer has one type B repeat unit, one type C repeat unit, and two different type G repeat units, is at least a tetrapolymer, and the one type B repeat unit is derived from maleic acid, the one type C repeat unit is derived from itaconic acid, and the two type G repeat units are respectively derived from methallylsulfonic acid and allylsulfonic acid.

More generally, the invention provides potassium products comprising at least partially water soluble potassium-containing solids having thereon the dried residue of an aqueous additive comprising a polymer including at least four repeat units distributed along the polymer chain, the repeat units including at least one each of a maleic, itaconic, and sulfonate repeat unit.

The polymers of the invention may be in the acid form or as partial or complete salts of alkali metals. The polymers are normally in the form of aqueous dispersions and are as such applied to the potassium solids, followed by drying thereof, so that the polymer is in the form of a dried residue. The potassium products of the invention may be used by applying the products to soil.

8. Seed Products

Improved coated seed products are also a part of the invention and comprise an agricultural seed coated with a polymer composition, the polymer composition including an anionic polymer comprising at least four repeat units distributed along the length of the polymer chain, the at least four repeat units including at least one each of type B, type C, and type G repeat units, the type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat units may be substituted with one or more C1-C6 straight or branched chain alkyl groups substantially free of ring structures and halo atoms, and wherein the salts have salt-forming cations selected from the group consisting of metals, amines, and mixtures thereof, the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more C1-C6 straight or branched chain alkyl groups substantially free of ring structures and halo atoms, and wherein the salts have salt-forming cations selected from the group consisting of metals, amines, and mixtures thereof, the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more C1-C6 straight or branched chain alkyl groups substantially free of ring structures and halo atoms, and wherein the salts of the type G repeat units have salt-forming cations selected from the group consisting of metals, amines, and mixtures thereof, the anionic polymer containing no more than about 10 mole percent of non-carboxylate olefins and/or ethers.

The polymer composition is present in the seed product at a level of from about 0.001-10% by weight, based upon the total weight of the coated seed product. Preferably, at least about 96 mole percent of the repeat units in the polymer are selected from the group consisting of type B, C, and G repeat units, and mixtures thereof, and most preferably the repeat units consist essentially of repeat units selected from the group consisting of type B, C, and G repeat units, and mixtures thereof; also, it is preferred that the polymers be substantially free of ester and noncarboxylate olefin groups. Particularly advantageous polymers have one type B repeat unit, one type C repeat unit, and two different type G repeat units, and especially where the polymer is a tetrapolymer, the one type B repeat unit is derived from maleic acid, the one type C repeat unit is derived from itaconic acid, and two type G repeat units are respectively derived from methallylsulfonic acid and allylsulfonic acid.

Certain preferred polymers have type B repeat unit present at a level of from about 35-50 mole percent, the type C repeat unit present at a level of from about 20-55 mole percent, the type G repeat unit derived from methallylsulfonic acid being present at a level of from about 1-25 mole percent, and the type G repeat unit derived from allylsulfonic acid being present at a level of from about 1-20 mole percent, where the total amount of all of the repeat units in the polymer is taken as 100 mole percent.

The polymers useful in the invention may be in acid form or as partial or complete salts, particularly of micronutrient metals (e.g., Zn, Mn, B, Fe, Mo, Cu, and mixtures thereof).

More generally, the invention provides an agricultural seed coated with a polymer composition, the polymer composition including an anionic polymer comprising at least four repeat units distributed along the length of the polymer chain, the repeat units including at least one each of a maleic, itaconic, and sulfonate repeat unit.

In preparing the seed products of the invention, the polymer is initially applied to the seed as an aqueous composition, preferably having a pH of from about 5-7.

9. Methods of Reducing Atmospheric Ammonia

The invention additionally provides a method of reducing atmospheric ammonia by applying a polymer composition in an area subject to evolution of ammonia, the polymer composition including an anionic polymer comprising at least four repeat units distributed along the length of the polymer chain, the repeat units including at least one each of a maleic, itaconic, and sulfonate repeat unit. The area may be a livestock or poultry confinement facility including a manure collection zone, upright walls forming an enclosure, and a roof substantially covering the zone, and in such cases, the polymer composition may be applied directly to the manure within the collection zone. The polymer composition is preferably applied at a level of from about 0.005-3 gallons per ton of manure, in the form of an aqueous dispersion having a pH of from about 1-5. If desired, another polymer may be used in combination with the anionic polymer and including maleic and itaconic repeat units. The polymers of the invention may be in the form of a partial or complete salt, particularly a calcium and/or ammonium partial salt. Moreover, certain preferred polymer compositions include a first polymer in the form of a partial salt of calcium, and a second polymer in the form of a partial salt of ammonium.

Most preferably, the repeat units of the polymer include at least one each of type B, type C, and type G repeat units,
  the type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat units may be substituted with one or more C1-C6 straight or branched chain alkyl groups substantially free of ring structures and halo atoms, and wherein the salts have salt-forming cations selected from the group consisting of metals, amines, and mixtures thereof,
  the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more C1-C6 straight or branched chain alkyl groups substantially free of ring structures and halo atoms, and wherein the salts have salt-forming cations selected from the group consisting of metals, amines, and mixtures thereof,
  the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more C1-C6 straight or branched chain alkyl groups substantially free of ring structures and halo atoms, and wherein the salts of the type G repeat units have salt-forming cations selected from the group consisting of metals, amines, and mixtures thereof,
  at least about 90 mole percent of the repeat units therein are selected from the group consisting of type B, C, and G repeat units, and mixtures thereof,
  the repeat units being randomly located along the polymer,
  the polymer containing no more than about 10 mole percent of any of (I) non-carboxylate olefin repeat units, (ii) ether repeat units, and (iii) non-sulfonated monocarboxylic repeat units.

This polymer preferably has at least about 96 mole percent of the repeat units therein selected from the group consisting of type B, C, and G repeat units, and mixtures thereof, and most preferably consists essentially of repeat units selected from the group consisting of type B, C, and G repeat units, and mixtures thereof. These polymers are preferably substantially free of ester and noncarboxylate olefin groups. One preferred polymer has one type B repeat unit, one type C repeat unit, and two different type G repeat units. In this case, the polymer is preferably a tetrapolymer with the one type B repeat unit derived from maleic acid, the one type C repeat unit derived from itaconic acid, and the two type G repeat units respectively derived from methallylsulfonic acid and allylsulfonic acid. Furthermore, the type B repeat unit is present at a level of from about 35-50 mole percent, the type C repeat unit is present at a level of from about 20-55 mole percent, the type G repeat unit derived from methallylsulfonic acid is present at a level of from about 1-25 mole percent, and the type G repeat unit derived from allylsulfonic acid being present at a level of from about 1-20 mole percent, where the total amount of all of the repeat units in the polymer is taken as 100 mole percent.

Additional preferred compositions are operable to reduce atmosphere ammonia by application of the composition to an area subject to evolution of ammonia, with such composition comprising a first polymer composition comprising a first anionic polymer having at least four repeat units distributed along the length of the polymer chain, the repeat units including at least one each of a maleic, itaconic, and sulfonate repeat unit, the first anionic polymer being in the form of a partial or complete salt of calcium; and a second polymer composition comprising a second anionic polymer having maleic and itaconic repeat units along the length of the polymer chain, the second anionic polymer being a partial or complete salt of ammonium. Such polymers preferably are each in the form of an aqueous dispersion and have at least four repeat units distributed along the length of the polymer chain, the repeat units including at least one each of a maleic, itaconic, and sulfonate repeat unit.

10. Improved Animal Feeds and Waters

Improved animal feeds are provided comprising quantities of feed ingredients normally fed to the animal, and an amount of a feed amendment including a partial or complete polymer salt, the amount of the amendment sufficient to reduce volatilized ammonia derived from the excrement of the animal fed the improved animal feed, as compared with the volatilized ammonia of an animal fed an identical feed, without the amendment. The polymer salts of the invention are usually in the form of aqueous dispersions having a pH of from about 1-5 and comprise at least four repeat units distributed along the length of the polymer chain, the repeat units including at least one each of a maleic, itaconic, and sulfonate repeat unit.

In preferred forms, the at least four repeat units include at least one each of type B, type C, and type G repeat units,
  the type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat units may be substituted with one or more C1-C6 straight or branched chain alkyl groups substantially free of ring structures and halo atoms, and wherein the salts have salt-forming cations selected from the group consisting of metals, amines, and mixtures thereof,
  the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more C1-C6 straight or branched chain alkyl groups substantially free of ring structures and halo atoms, and wherein the salts have salt-forming cations selected from the group consisting of metals, amines, and mixtures thereof, the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more C1-C6 straight or branched chain alkyl groups substantially free of ring structures and halo atoms, and wherein the salts of the type G repeat units have salt-forming cations selected from the group consisting of metals, amines, and mixtures thereof, at least about 90 mole percent of the repeat units therein are selected from the group consisting of type B, C, and G repeat units, and mixtures thereof, the repeat units being randomly located along the polymer, the polymer salt containing no more than about 10 mole percent of any of (I) non-carboxylate olefin repeat units, (ii) ether repeat units, and (iii) non-sulfonated monocarboxylic repeat units.

Advantageously, at least about 96 mole percent of the repeat units therein are selected from the group consisting of type B, C, and G repeat units, and mixtures thereof, and even more preferably the repeat units consist essentially of type B, C, and G repeat units, and mixtures thereof; moreover, the polymers are preferably substantially free of ester and noncarboxylate olefin groups.

Specially preferred polymer salts have one type B repeat unit, one type C repeat unit, and two different type G repeat units, and, when in the form of a tetrapolymer, the one type B repeat unit is derived from maleic acid, the one type C repeat unit is derived from itaconic acid, and the two type G repeat units are respectively derived from methallylsulfonic acid and allylsulfonic acid. These polymer salts preferably have the type B repeat unit being present at a level of from about 35-50 mole percent, the type C repeat unit being present at a level of from about 20-55 mole percent, the type G repeat unit derived from methallylsulfonic acid being present at a level of from about 1-25 mole percent, and the type G repeat unit derived from allylsulfonic acid being present at a level of from about 1-20 mole percent, where the total amount of all of the repeat units in the polymer is taken as 100 mole percent.

In many cases, two separate polymer salts are used, one being a partial salt of calcium, and the other being a partial salt of ammonium. Moreover, other, different polymers including maleic and itaconic repeat units may be used in the amendments of the invention.

The animal feeds of the invention may be used as a method of reducing volatilized ammonia derived from the excrement of animals, comprising the step of administering to (feeding) the animals one or more of the above-described feeds.

Similarly, the invention also provides improved animal waters comprising a mixture of water and a partial or complete polymer salt, the polymer salt being in an amount sufficient to reduce volatilized ammonia derived from the excrement of the animal fed the improved animal water, as compared with the volatilized ammonia of an animal fed an identical water, without the amendment. The polymer salts preferably are in the form of aqueous dispersions having a pH of from about 1-5, and comprise at least four repeat units distributed along the length of the polymer chain, the repeat units including at least one each of a maleic, itaconic, and sulfonate repeat unit.

The at least four repeat units preferably include at least one each of type B, type C, and type G repeat units, the type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat units may be substituted with one or more C1-C6 straight or branched chain alkyl groups substantially free of ring structures and halo atoms, and wherein the salts have salt-forming cations selected from the group consisting of metals, amines, and mixtures thereof, the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more C1-C6 straight or branched chain alkyl groups substantially free of ring structures and halo atoms, and wherein the salts have salt-forming cations selected from the group consisting of metals, amines, and mixtures thereof, the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more C1-C6 straight or branched chain alkyl groups substantially free of ring structures and halo atoms, and wherein the salts of the type G repeat units have salt-forming cations selected from the group consisting of metals, amines, and mixtures thereof, at least about 90 mole percent of the repeat units therein are selected from the group consisting of type B, C, and G repeat units, and mixtures thereof, the repeat units being randomly located along the polymer, the polymer salt containing no more than about 10 mole percent of any of (I) non-carboxylate olefin repeat units, (ii) ether repeat units, and (iii) non-sulfonated monocarboxylic repeat units.

Advantageously, at least about 96 mole percent of the repeat units therein are selected from the group consisting of type B, C, and G repeat units, and mixtures thereof, and more preferably the repeat units consist essentially of the type B, C, and G repeat units, and mixtures thereof; the polymers are also preferably substantially free of ester and noncarboxylate olefin groups.

In one preferred case, the polymer salt has one type B repeat unit, one type C repeat unit, and two different type G repeat units, and especially where the polymer salt is a tetrapolymer, the one type B repeat unit is derived from maleic acid, the one type C repeat unit is derived from itaconic acid, and the two type G repeat units are respectively derived from methallylsulfonic acid and allylsulfonic acid. The type B repeat unit is preferably present at a level of from about 35-50 mole percent, the type C repeat unit being present at a level of from about 20-55 mole percent, the type G repeat unit derived from methallylsulfonic acid being present at a level of from about 1-25 mole percent, and the type G repeat unit derived from allylsulfonic acid being present at a level of from about 1-20 mole percent, where the total amount of all of the repeat units in the polymer is taken as 100 mole percent.

The polymers of the invention are preferably in the form of partial salts, and the overall compositions may comprise two separate polymer salts, one polymer salt being a partial salt of calcium, and the other polymer salt being a partial salt of ammonium.

11. Methods of Improving Soil Conditions

The invention provides methods of inhibiting a soil condition selected from the group consisting of nitrification processes, phosphate fixation processes, urease activities, and combinations thereof, comprising the step of applying to soil an effective amount of an anionic polymer including at least four repeat units distributed along the length of the polymer chain, the repeat units including at least one each of a maleic, itaconic, and sulfonate repeat units. The repeat units preferably include at least one each of type B, type C, and type G repeat units, the type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein type B repeat units may be substituted with one or more C1-C6 straight or branched chain alkyl groups substantially free of ring structures and halo atoms, and wherein the salts have salt-forming cations selected from the group consisting of metals, amines, and mixtures thereof, the type C repeat units selected from the group consisting of repeat units derived from substituted or unsubstituted monomers of itaconic acid, itaconic anhydride, and any isomers, esters, and the partial or complete salts of any of the foregoing, and mixtures of any of the foregoing, wherein the type C repeat units may be substituted with one or more C1-C6 straight or branched chain alkyl groups substantially free of ring structures and halo atoms, and wherein the salts have salt-forming cations selected from the group consisting of metals, amines, and mixtures thereof, the type G repeat units selected from the group consisting of repeat units derived from substituted or unsubstituted sulfonated monomers possessing at least one carbon-carbon double bond and at least one sulfonate group and which are substantially free of aromatic rings and amide groups, and any isomers, and the partial or complete salts of any of the foregoing, and mixtures of any of the foregoing, wherein type G repeat units may be substituted with one or more C1-C6 straight or branched chain alkyl groups substantially free of ring structures and halo atoms, and wherein the salts of the type G repeat units have salt-forming cations selected from the group consisting of metals, amines, and mixtures thereof, at least about 90 mole percent of the repeat units therein are selected from the group consisting of type B, C, and G repeat units, and mixtures thereof, the repeat units being randomly located along the polymer, the polymer containing no more than about 10 mole percent of any of (I) non-carboxylate olefin repeat units, (ii) ether repeat units, and (iii) non-sulfonated monocarboxylic repeat units.

Advantageously, at least about 96 mole percent of the repeat units therein are selected from the group consisting of type B, C, and G repeat units, and mixtures thereof, and more preferably the repeat units consist essentially of type B, C, and G repeat units, and mixtures thereof; the polymers are substantially free of ester and noncarboxylate olefin groups.

In one particular case, the polymer has one type B repeat unit, one type C repeat unit, and two different type G repeat units; especially where the polymer is a tetrapolymer, the one type B repeat unit is derived from maleic acid, the one type C repeat unit is derived from itaconic acid, and two type G repeat units are respectively derived from methallylsulfonic acid and allylsulfonic acid.

In preferred forms, the type B repeat unit is present at a level of from about 35-50 mole percent, the type C repeat unit being present at a level of from about 20-55 mole percent, the type G repeat unit derived from methallylsulfonic acid being present at a level of from about 1-25 mole percent, and the type G repeat unit derived from allylsulfonic acid being present at a level of from about 1-20 mole percent, where the total amount of all of the repeat units in the polymer is taken as 100 mole percent.

In carrying out the invention, the anionic polymer is mixed with an ammoniacal solid, liquid, or gaseous fertilizer, and especially solid fertilizers; in the latter case, the polymer is applied to the surface of the fertilizer as an aqueous dispersion followed by drying, so that the polymer is present on the solid fertilizer as a dried residue. The polymer is generally applied at a level of from about 0.01-10% by weight, based upon the total weight of the polymer/fertilizer product taken as 100% by weight. Where the fertilizer is an aqueous liquid fertilizer, the polymer is added thereto with mixing.

The polymers of the invention are preferably in aqueous dispersion and have a pH of up to about 3. These polymers may be used alone or in combination with another anionic polymer including maleic and itaconic repeat units.

DETAILED DESCRIPTION OF THE PREFERRED EMBODIMENTS

The Novel Polymers of the Invention

The novel polyanionic polymers of the present invention (sometimes referred to herein as "Class I" polymers) are at least tetrapolymers, i.e., they are composed of at least four different repeat units individually and independently selected from the group consisting of type B, type C, and type G repeat units, and mixtures thereof, described in detail below. However, the polymers comprehend polymers having more than four distinct repeat units, with the excess repeat units being selected from the group consisting of type B, type C, and type G repeat units, and mixtures thereof, as well as other monomers or repeat units not being type B, C, or G repeat units.

Preferred polymers contain at least one repeat unit from each of the B, C, and G types, one other repeat unit selected from the group consisting of type B, type C, and type G repeat units, and optionally other repeat units not selected from type B, type C, and type G repeat units. Particularly preferred polymers comprise a single type B repeat unit, a single type C repeat unit, and two different type G repeat units, or two different type B repeat units, a single type C repeat unit, and one or more different type G repeat units.

However constituted, preferred polymers contain at least about 90 mole percent (more preferably at least about 96 mole percent) of repeat units selected from the group consisting of type B, C, and G repeat units (i.e., the polymers should contain no more than about 10 mole percent (preferably no more than about 4 mole percent) of repeat units not selected from types B, C, and G). The most preferred final polymers should be substantially free of ester groups (i.e., no more than about 5 mole percent ester groups, more preferably no more than about 1 mole percent).

The polymers may be converted to a wide range of salts, whether fully saturated (wherein all anionic groups are paired with a suitable cation, e.g., a metal or amine) or partial (wherein not all anionic groups are so paired), and may be made using either a single cation (e.g., sodium), or using any number of different cations at any level (e.g., mixed sodium and ammonium cations). Metal cations can be simple cations such as sodium or calcium, but more complex cations can also be used, such as cations containing a metal atom and other atom(s) as well, e.g., vanadyl cations. Among preferred metal cations (to be used alone or as mixed salts) are those derived from alkali, alkaline earth, and transition metals. The polymers may also be in the form of amine partial or complete salts (as used herein, "amines" refers to primary, secondary, or tertiary amines, monoamines, diamines, and triamines, as well as ammonia, ammonium ions, quaternary amines, quaternary ammonium ions, alkanolamines (e.g., ethanolamine, diethanolamine, and triethanolamine), and tetraalkylammonium species). The most preferred class of amines are alkyl amines, where the alkyl group(s) have from 1-30 carbon atoms and are of straight or branched chain configuration. Such amines should be essentially free of aromatic rings (no more than about 5 mole percent aromatic rings, and more preferably no more than about 1 mole percent thereof). A particularly suitable alkyl amine is isopropylamine.

The degree of cation substitution and the identity of cation(s) may be varied completely independently of each other. This flexibility allows production of many different full or partial salt polymers of desirable properties. The solubility and other properties of the polymers can be modified by judicious selection of the types and amounts of salt-forming cations. For example, by increasing the level of divalent cations (e.g., Ca, Mg) and elevating the pH of aqueous dispersions of the polymers above pH 1, the resultant polymer salts are especially useful as films and coatings.

1. Type B Repeat Units

Type B repeat units in accordance with the invention are dicarboxylate repeat units derived from monomers of maleic acid and/or anhydride, fumaric acid and/or anhydride, mesaconic acid and/or anhydride, substituted maleic acid and/or anhydride, substituted fumaric acid and/or anhydride, substituted mesaconic acid and/or anhydride, mixtures of the foregoing, and any isomers, esters, acid chlorides, and partial or complete salts of any of the foregoing. As used herein with respect to the type B repeat units, "substituted" species refers to alkyl substituents (preferably C1-C6 straight or branched chain alkyl groups substantially free of ring structures), and halo substituents (i.e., no more than about 5 mole percent of either ring structures or halo substituents, preferably no more than about 1 mole percent of either); the substituents are normally bound to one of the carbons of a carbon-carbon double bond of the monomer(s) employed. Similarly, the "salts" of the type B repeat units refers to partial or complete salts prepared using salt-forming cations selected from the group consisting of metals, amines, and mixtures thereof. In preferred forms, the total amount of type B repeat units in the polymers of the invention should range from about 1-70 mole percent, more preferably from about 20-65 mole percent, and most preferably from about 35-55 mole percent, where the total amount of all of the repeat units in the polymer is taken as 100 mole percent.

Maleic acid, methylmaleic acid, maleic anhydride, methylmaleic anhydride, and mesaconic acid (either alone or as various mixtures) are the most preferred monomers for generation of type B repeat units. Those skilled in the art will appreciate the usefulness of in situ conversion of acid anhydrides to acids in a reaction vessel just before or even during a reaction. However, it is also understood that when corresponding esters (e.g., maleic or citraconic esters) are used as monomers during the initial polymerization, this should be followed by hydrolysis (acid or base) of pendant ester groups to generate a final carboxylated polymer substantially free of ester groups.

2. Type C Repeat Units

Type C repeat units in accordance with the invention are derived from monomers of itaconic acid and/or anhydride, substituted itaconic acid and/or anhydride, as well as isomers, esters, acid chlorides, and partial or complete salts of any of the foregoing. The type C repeat units are present in the preferred polymers of the invention at a level of from about 1-80 mole percent, more preferably from about 15-75 mole percent, and most preferably from about 20-55 mole percent, where the total amount of all of the repeat units in the polymer is taken as 100 mole percent.

The itaconic acid monomer used to form type C repeat unit has one carboxyl group, which is not directly attached to the unsaturated carbon-carbon double bond used in the polymerization of the monomer. Hence, the preferred type C repeat unit has one carboxyl group directly bound to the polymer backbone, and another carboxyl group spaced by a carbon atom from the polymer backbone. The definitions and discussion relating to "substituted," "salt," and useful salt-forming cations (metals, amines, and mixtures thereof) with respect to the type C repeat units, are the same as those set forth for the type B repeat units.

Unsubstituted itaconic acid and itaconic anhydride, either alone or in various mixtures, are the most preferred monomers for generation of type C repeat units. Again, if itaconic anhydride is used as a starting monomer, it is normally useful to convert the itaconic anhydride monomer to the acid form in a reaction vessel just before or even during the polymerization reaction. Any remaining ester groups in the polymer are normally hydrolyzed, so that the final carboxylated polymer is substantially free of ester groups.

3. Type G Repeat Units

Type G repeat units in accordance with the invention are derived from substituted or unsubstituted sulfonate-bearing monomers possessing at least one carbon-carbon double bond and at least one sulfonate group, in acid, partial or complete salt, or other form, and which are substantially free of aromatic rings and amide groups (i.e., no more than about 5 mole percent of either aromatic rings or amide groups, preferably no more than about 1 mole percent of either). The type G repeat units are preferably selected from the group consisting of C1-C8 straight or branched chain alkenyl sulfonates, substituted forms thereof, and any isomers or salts of any of the foregoing; especially preferred are alkenyl sulfonates selected from the group consisting of vinyl, allyl, and methallylsulfonic acids or salts. The total amount of type G repeat units in the polymers of the invention should range from about 0.1-65 mole percent, more preferably from about 1-35 mole percent, and most preferably from about 1-25 mole percent, where the total amount of all of the repeat units in the polymer is taken as 100 mole percent. The definitions and discussion relating to "substituted," "salt," and useful salt-forming cations (metals, amines, and mixtures thereof) with respect to the type G repeat units, are the same as those set forth for the type B repeat units.

Vinylsulfonic acid, allylsulfonic acid, and methallylsulfonic acid, either alone or in various mixtures, are deemed to be the most preferred monomers for generation of type G repeat units. It has also been found that alkali metal salts of these acids are also highly useful as monomers. In this connection, it was unexpectedly discovered that during polymerization reactions yielding the novel polymers of the invention, the presence of mixtures of alkali metal salts of these monomers with acid forms thereof does not inhibit completion of the polymerization reaction. By the same token, mixtures of monomers of maleic acid, itaconic acid, sodium allyl sulfonate, and sodium methallyl sulfonate do not inhibit the polymerization reaction.

Further Preferred Characteristics of the Novels Polymers

As noted previously, the total abundance of type B, C, and G repeat units in the polymers of the invention is preferably at least about 90 mole percent, more preferably at least about 96 mole percent, and most preferably the polymers consist essentially of or are 100 mole percent B, C, and G-type repeat units. It will be understood that the relative amounts and identities of polymer repeat units can be varied, depending upon the specific properties desired in the resultant polymers. Moreover, it is preferred that the polymers of the invention contain no more than about 10 mole percent (more preferably no more than about 5 mole percent) of any of (I) non-carboxylate olefin repeat units, (ii) ether repeat units, (iii) ester repeat units, (iv) non-sulfonated monocarboxylic repeat units, and (v) amide-containing repeat units. "Non-carboxylate" and "non-sulfonated" refers to repeat units having essentially no carboxylate groups or sulfonate groups in the corresponding repeat units. Advantageously, the mole ratio of the type B and type C repeat units in combination to the type G repeat units (that is, the mole ratio of (B+C)/G) should be from about 0.5-20:1, more preferably from about 2:1-20:1, and still more preferably from about 2.5:1-10:1. Still further, the polymers should be essentially free (e.g., less than about 1 mole percent) of alkyloxylates or alkylene oxide (e.g., ethylene oxide)-containing repeat units, and most desirably entirely free thereof.

The preferred polymers of the invention have the repeat units thereof randomly located along the polymer chain without any ordered sequence of repeat units. Thus, the polymers hereof are not, e.g., alternating with different repeat units in a defined sequence along the polymer chain.

It has also been determined that the preferred polymers of the invention should have a very high percentage of the repeat units thereof bearing at least one anionic group, e.g., at least about 80 mole percent, more preferably at least about 90 mole percent, still more preferably at least about 95 mole percent, and most preferably essentially all of the repeat units contain at least one anionic group. It will be appreciated that the B and C repeat units have two anionic groups per repeat unit, whereas the preferred sulfonate repeat units have one anionic group per repeat unit.

For a variety of applications, certain tetrapolymer compositions are preferred, i.e., a preferred polymer backbone composition range (by mole percent, using the parent monomer names of the corresponding repeat units) is: maleic acid 35-50%; itaconic acid 20-55%; methallylsulfonic acid 1-25%; and allylsulfonic sulfonic acid 1-20%, where the total amount of all of the repeat units in the polymer is taken as 100 mole percent. It has also been found that even small amounts of repeat units, which are neither B nor C repeat units, can significantly impact the properties of the final polymers, as compared with prior BC polymers. Thus, even 1 mole percent of each of 2 different G repeat units can result in a tetrapolymer exhibiting drastically different behaviors, as compared with BC polymers.

The molecular weight of the polymers is also highly variable, again depending principally upon the desired properties. Generally, the molecular weight distribution for polymers in accordance with the invention is conveniently measured by size exclusion chromatography. Broadly, the molecular weight of the polymers ranges from about 800-50,000, and more preferably from about 1000-5000. For some applications, it is advantageous that at least 90% of the finished polymer be at or above a molecular weight of about 1000 measured by size exclusion chromatography in 0.1 M sodium nitrate solution via refractive index detection at 35° C. using polyethylene glycol standards. Of course, other techniques for such measurement can also be employed.

The polymers of the invention may be mixed with or complexed with metal or non-metal ions, and especially those selected from the group of simple cations such as the amines, alkali metals, Fe, Mn, Mg, Zn, Cu, Ni, Co, Mo, V, Cr, Si, B, Ca, and compounds containing these cations, e.g., boric acid, borates, molybdates, more complex cations such as vanadyl ions $[VO]^{2+}$, and other complex ions containing vanadium, and mixtures of any of the foregoing.

The polymers of the invention can also be used in formulations containing a wide variety of other ingredients, including but not limited to alcohols, diols, polyols, organic acids, polyvinyl alcohols, dyes, plastics, and mixtures thereof.

Syntheses of the Polymers of the Invention

Virtually any conventional method of free radical polymerization may be suitable for the synthesis of the polymers of the invention. However, a preferred and novel synthesis may be used, which is applicable not only for the production of the polymers of the invention, but also for the synthesis of polymers containing dicarboxylate repeat units and sulfonate repeat units and preferably containing at least one carbon-carbon double bond. Such types of polymers are disclosed in U.S. Pat. Nos. 5,536,311 and 5,210,163.

Generally speaking, the new synthesis methods comprise carrying out a free radical polymerization reaction between dicarboxylate and sulfonate repeat units in the presence of hydrogen peroxide and vanadium-containing species to achieve a conversion to polymer in excess of 90%, and more preferably in excess of 98%, by mole. That is, a dispersion of the dicarboxylate and sulfonated monomers is created and free radical initiator(s) are added followed by allowing the monomers to polymerize.

Of course, the preferred dicarboxylate and sulfonate repeat units are those described previously as B, C, and G repeat units. Moreover, it has been found that acceptable polymers can be synthesized having relatively low amounts of maleic-type B repeat units, without creating excess unreacted monomers. U.S. Pat. No. 5,135,677 describes synthesis of polymers containing maleic acid and other water soluble repeat units. The '677 patent teaches that the amount of maleic repeat units is at least 50 weight percent, more preferably at least 75 weight percent, and that if smaller amounts of maleic repeat units are employed, large amounts of residual monomers are created and the resultant polymers are poor in biodegradability. However, it has been found that by judicious selection of the B, C, and G repeat units of the invention, essentially complete polymerization is achieved even with maleic-type B repeat units below 50 mole percent of the reaction mixture, as noted previously.

Preferably, hydrogen peroxide is the sole initiator used in the reaction, but in any case, it is advantageous to conduct the reaction in the absence of any substantial quantities of other initiators (i.e., the total weight of the initiator molecules used should be about 95% by weight hydrogen peroxide, more preferably about 98% by weight, and most preferably 100% by weight thereof). Various sources of vanadium may be employed, with vanadium oxysulfates being preferred.

It has been discovered that it is most advantageous to perform these polymerization reactions in substantially aqueous dispersions (e.g., the dispersants are at least about 95% by weight water, more preferably at least about 98% by weight water, and most preferably 100% by weight water). The aqueous dispersions may also contain additional monomer(s), but only to the minor extent noted.

It has also been found that the preferred polymerization reactions may be carried out without the use of inert atmospheres, e.g., in an ambient air environment. As is well known in the art, free radical polymerization reactions in dispersions are normally conducted in a way that excludes the significant presence of oxygen. As a result, these prior techniques involve such necessary and laborious steps as degassing, inert gas blanketing of reactor contents, monomer treatments to prevent air from being present, and the like. These prior expedients add to the cost and complexity of the polymerizations, and can present safety hazards. However, in the polymerizations of the polymers of the present invention, no inert gas or other related steps are required, although they may be employed if desired.

One preferred embodiment comprises creating highly concentrated aqueous dispersions of solid monomer particles (including saturated dispersions containing undissolved monomers) at a temperature of from about 50-125° C., more preferably from about 75-110° C., and adding vanadium oxysulfate to give a vanadium concentration in the dispersion of from about 1-1000 ppm, and more preferably from about 5-500 ppm (metals basis). This is followed by the addition of hydrogen peroxide over a period of from about 30 minutes-24 hours (more preferably from about 1-5 hours) in an amount effective to achieve polymerization. This process is commonly carried out in a stirred tank reactor equipped with facilities for controlling temperature and composition, but any suitable equipment used for polymerization may be employed.

Another highly preferred and efficient embodiment involves charging a stirred tank reactor with water, followed by heating and the addition of monomers to give a dispersion having from about 40-75% w/w solids concentration. Where maleic and/or itaconic monomers are employed, they may be derived either from the corresponding acid monomers, or from in situ conversion of the anhydrides to acid in the water. Carboxylate and sulfonated monomers are preferred in their acid and/or anhydride form, although salts may be used as well. Surprisingly, it has been found that incomplete monomer dissolution is not severely detrimental to the polymerization; indeed, the initially undissolved fraction of monomers will dissolve at some time after polymerization has been initiated.

After the initial heating and introduction of monomers, the reactor contents are maintained at a temperature between about 80-125° C., with the subsequent addition of vanadium oxysulfate. Up to this point in the reaction protocol, the order of addition of materials is not critical. After introduction of vanadium oxysulfate, a hydrogen peroxide solution is added over time until substantially all of the monomers are converted to polymer. Peroxide addition may be done at a constant rate, a variable rate, and with or without pauses, at a fixed or variable temperature. The concentration of peroxide solution used is not highly critical, although the concentration on the low end should not dilute the reactor contents to the point where the reaction becomes excessively slow or impractically diluted. On the high end, the concentration should not cause difficulties in performing the polymerization safely in the equipment being used.

After the polymerization is completed, the cations present may be left as they are, or additional cations may be added. For example, the reactor contents may be neutralized to a higher pH by the addition of various alkali metal or alkaline earth metal cations, ammonia, amines, or any other suitable cation source, thereby providing various mixed salts of the polymer, if desired.

Preferably, the polymerization reactions of the invention are carried out to exclude substantial amounts of dissolved iron species (i.e., more than about 5% by weight of such species, and more preferably substantially less, on the order of below about 5 ppm, and most advantageously under about 1 ppm). This is distinct from certain prior techniques requiring the presence of iron-containing materials. Nonetheless, it is acceptable to carry out the polymerization of the invention in 304 or 316 stainless steel reactors. It is also preferred to exclude from the polymerization reaction any significant amounts (nor more than about 5% by weight) of the sulfate salts of ammonium, amine, alkali and alkaline earth metals, as well as their precursors and related sulfur-containing salts, such as bisulfites, sulfites, and meta-bisulfites. It has been found that use of these sulfate-related compounds leaves a relatively high amount of sulfates and the like in the final polymers, which either must be separated or left as a product contaminant.

The high polymerization efficiencies of the preferred syntheses result from the use of water as a solvent and without the need for other solvents, elimination of other initiators (e.g., azo, hydroperoxide, persulfate, organic peroxides) iron and sulfate ingredients, the lack of recycling loops, so that substantially all of the monomers are converted to the finished polymers in a single reactor. This is further augmented by the fact that the polymers are formed first, and subsequently, if desired, partial or complete salts can be created. The important factors are the simultaneous presence of water solvent, peroxide initiator, vanadium compound, and monomers provided at appropriate times and at useful temperatures. This can be arranged in any equipment and in any fashion known in the art, i.e., the manor in which this is arranged is not critical. For example, a certain proportion of the monomers may be in water solution in a reaction vessel, while additional monomers and peroxide are added to the vessel as the reaction proceeds in the presence of appropriate vanadium compound levels.

EXAMPLES

The following Examples 1-4 describe preferred synthesis techniques for preparing polymers; it should be understood, however, that these Examples are provided by way of illustration only and nothing therein should be taken as a limitation on the overall scope of the invention.

Example 1—Exemplary Synthesis

Apparatus:

A cylindrical reactor was used, capable of being heated and cooled, and equipped with efficient mechanical stirrer, condenser, gas outlet (open to atmosphere), solids charging port, liquids charging port, thermometer and peroxide feeding tube.

Procedure: Water was charged into the reactor, stirring was initiated along with heating to a target temperature of 95° C. During this phase, itaconic acid, sodium methallylsulfonate, sodium allylsulfonate, and maleic anhydride were added so as to make a 50% w/w solids dispersion with the following monomer mole fractions:

maleic: 45%
itaconic: 35%
methallylsulfonate: 15%
allylsulfonate: 5%

When the reactor temperature reached 95° C., vanadium oxysulfate was added to give a vanadium metal concentration of 25 ppm by weight. After the vanadium salt fully dissolved, hydrogen peroxide (as 50% w/w dispersion) was added continuously over 3 hours, using the feeding tube. The total amount of hydrogen peroxide added was 5% of the dispersion weight in the reactor prior to peroxide addition. After the peroxide addition was complete, the reactor was held at 95° C. for two hours, followed by cooling to room temperature.

The resulting polymer dispersion was found to have less than 2% w/w total of residual monomers as determined by chromatographic analysis.

Example 2—Exemplary Synthesis

Apparatus:
Same as Example 1

Procedure: Water was charged into the reactor, stirring was initiated along with heating to a target temperature of 100° C. During this phase, itaconic acid, sodium methallylsulfonate, sodium allylsulfonate, and maleic anhydride were added so as to make a 70% w/w solids dispersion with the following monomer mole fractions:

maleic: 45%
itaconic: 50%
methallylsulfonate: 4%
allylsulfonate: 1%

When the reactor temperature reached 100° C., vanadium oxysulfate was added to give a vanadium metal concentration of 25 ppm by weight. After the vanadium salt fully dissolved, hydrogen peroxide (as 50% w/w dispersion) was added continuously over 3 hours, using the feeding tube. The total amount of hydrogen peroxide added was 7.5% of the dispersion weight in the reactor prior to peroxide addition. After the peroxide addition was complete, the reactor was held at 100° C. for two hours, followed by cooling to room temperature.

The resulting polymer dispersion was found to have less than 1% w/w total of residual monomers as determined by chromatographic analysis.

Example 3—Exemplary Synthesis

A terpolymer salt dispersion containing 70% by weight polymer solids in water was prepared using a cylindrical reactor capable of being heated and cooled, and equipped with an efficient mechanical stirrer, a condenser, a gas outlet open to the atmosphere, respective ports for charging liquids and solids to the reactor, a thermometer, and a peroxide feeding tube.

Water (300 g) was charged into the reactor with stirring and heating to a target temperature of 95° C. During heating, itaconic acid, sodium methallylsulfonate, and maleic anhydride were added so as to make a 75% w/w solids dispersion with the following monomer mole fractions: maleic anhydride—20%; itaconic acid—60%; methallylsulfonate sodium salt—20%. When the monomers were initially added, they were in suspension in the water. As the temperature rose, the monomers became more fully dissolved before polymerization was initiated, and the maleic anhydride was hydrolyzed to maleic acid. When the reactor temperature reached 95° C., vanadium oxysulfate was added to yield a vanadium metal concentration of 50 ppm by weight of the reactor contents at the time of addition of the vanadium salt. After the vanadium salt fully dissolved, hydrogen peroxide was added as a 50% w/w dispersion in water continuously over two hours. At the time of hydrogen peroxide addition, not all of the monomers were completely dissolved, achieving what is sometimes referred to as "slush polymerization"; the initially undissolved monomers were subsequently dissolved during the course of the reaction. The total amount of hydrogen peroxide added equaled 5% of the dispersion weight in the reactor before addition of the peroxide.

After the peroxide addition was completed, the reaction mixture was held at 95° C. for two hours, and then allowed to cool to room temperature. The resulting polymer dispersion had a pH of slightly below 1.0 and was a partial sodium salt owing to the sodium cation on the sulfonate monomers. The dispersion was found to have a monomer content of less than 2% w/w, calculated as a fraction of the total solids in the reaction mixture, as determined by chromatographic analysis. Accordingly, over 98% w/w of the initially added monomers were converted to polymer.

Example 4—Preparation of Tetrapolymer Partial Salts

A tetrapolymer partial sodium salt dispersion containing 40% by weight polymer solids in water was prepared by the preferred free radical polymerization synthesis of the invention, using an aqueous reaction mixture having 45 mole percent maleic anhydride, 35 mole percent itaconic acid, 15 mole percent methallylsulfonate sodium salt, and 5 mole percent allylsulfonate. The final tetrapolymer dispersion had a pH of slightly below 1.0 and was a partial sodium salt owing to the sodium cation on the sulfonate monomers. At least about 90% of the monomers were polymerized in the reaction.

This sodium partial salt tetrapolymer was used to create a series of 40% solids in water partial salts. In each instance, apart from the sodium present in the tetrapolymer mixture, appropriate bases or base precursors (e.g., carbonates), or mixtures thereof were added to the aqueous tetrapolymer at room temperature to generate the corresponding salts. In all instances save for Salt A below, the in situ sodium resulting from the synthesis was the primary source of sodium used in the conversions; in Salt A, the bulk of the sodium came from the use of NaOH. Specifically, the following basic reactants were employed with quantities of the tetrapolymer to give the following salts:

Salt A—sodium hydroxide, pH 7.
Salt B—ammonium hydroxide and a minor amount of sodium hydroxide, pH 2.

Salt C—calcium carbonate and a minor amount of sodium hydroxide, pH 1.5.

Salt D—calcium carbonate and a minor amount of sodium hydroxide, pH 3.5.

Salt E—isopropylamine, pH 4.8.

Salt F—triethanolamine, pH 7.

Salt G—zinc carbonate, manganese carbonate, cupric basic carbonate, and sodium hydroxide, pH 6 (Zn content 2% by weight, Mn content 1% by weight, Cu content 250 ppm).

Salt H—zinc carbonate, pH 3 (Zn content 5% by weight).

Salt I—manganese carbonate, pH 4 (Mn content 5% by weight).

Mixtures of the Novel Polymers of the Invention with Other Polymers

The novel polymers hereof may be a part of polymer mixtures or fractions, which include other types of polymers, especially dicarboxylate polymers, and particularly those containing maleic and itaconic repeat units. These mixed polymer formulations may be used in all of the contexts hereafter described.

Preferred types of different polymers useful in the mixed polymer products are referred to as "Class IA" and "Class II" polymers.

Class IA Polymers

Class IA polymers contain both carboxylate and sulfonate functional groups, but are not the tetra- and higher order polymers of Class I. For example, terpolymers of maleic, itaconic, and allylsulfonic repeat units, which are per se known in the prior art, will function as the polyanionic polymer component of the compositions of the invention. The Class IA polymers thus are normally homopolymers, copolymers, and terpolymers, advantageously including repeat units individually and independently selected from the group consisting of type B, type C, and type G repeat units, without the need for any additional repeat units. Such polymers can be synthesized in any known fashion, and can also be produced using the previously described Class I polymer synthesis.

Class IA polymers preferably have the same molecular weight ranges and the other specific parameters (e.g., pH and polymer solids loading) previously described in connection with the Class I polymers, and may be converted to partial or complete salts using the same techniques described with reference to the Class I polymers. Class IA polymers are most advantageously synthesized using the techniques described above in connection with the Class I polymers.

Class IA Polymers

Class IA polymers contain both carboxylate and sulfonate functional groups, but are not the tetra- and higher order polymers of Class I. For example, terpolymers of maleic, itaconic, and allylsulfonic repeat units, which are per se known in the prior art, will function as the polyanionic polymer component of the compositions of the invention. The Class IA polymers thus are normally homopolymers, copolymers, and terpolymers, advantageously including repeat units individually and independently selected from the group consisting of type B, type C, and type G repeat units, without the need for any additional repeat units. Such polymers can be synthesized in any known fashion, and can also be produced using the previously described Class I polymer synthesis.

Class IA polymers preferably have the same molecular weight ranges and the other specific parameters (e.g., pH and polymer solids loading) previously described in connection with the Class I polymers, and may be converted to partial or complete salts using the same techniques described with reference to the Class I polymers. Class IA polymers are most advantageously synthesized using the techniques described above in connection with the Class I polymers.

Class II Polymers

Broadly speaking, the polyanionic polymers of this class are of the type disclosed in U.S. Pat. No. 8,043,995, which incorporated by reference herein in its entirety. The polymers include repeat units derived from at least two different monomers individually and respectively taken from the group consisting of what have been denominated for ease of reference as B' and C' monomers; alternately, the polymers may be formed as homopolymers or copolymers from recurring C' monomers. The repeat units may be randomly distributed throughout the polymer chains.

In detail, repeat unit B' is of the general formula

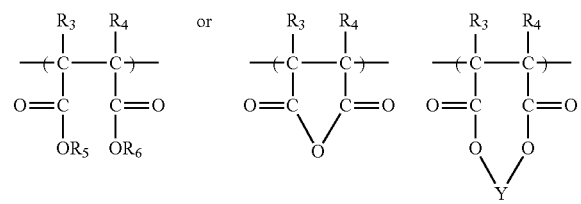

and repeat unit C' is of the general formula

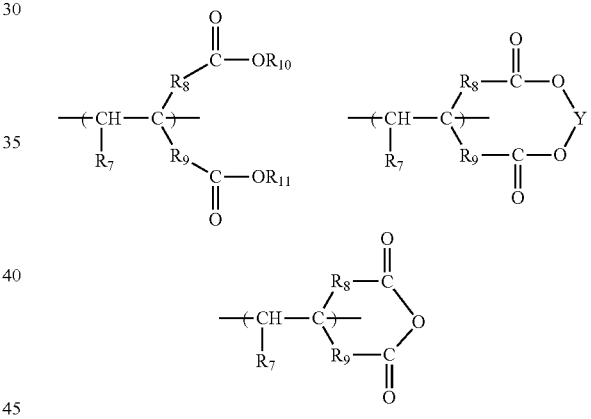

wherein each $R_7$ is individually and respectively selected from the group consisting of H, OH, $C_1$-$C_{30}$ straight, branched chain and cyclic alkyl or aryl groups, $C_1$-$C_{30}$ straight, branched chain and cyclic alkyl or aryl formate ($C_0$), acetate ($C_1$), propionate ($C_2$), butyrate ($C_3$), etc. up to $C_{30}$ based ester groups, $R'CO_2$ groups, OR' groups and COOX groups, wherein R' is selected from the group consisting of $C_1$-$C_{30}$ straight, branched chain and cyclic alkyl or aryl groups and X is selected from the group consisting of H, the alkali metals, $NH_4$ and the $C_1$-$C_4$ alkyl ammonium groups, $R_3$ and $R_4$ are individually and respectively selected from the group consisting of H, $C_1$-$C_{30}$ straight, branched chain and cyclic alkyl or aryl groups, $R_5$, $R_6$, $R_{10}$ and $R_{11}$ are individually and respectively selected from the group consisting of H, the alkali metals, $NH_4$ and the $C_1$-$C_4$ alkyl ammonium groups, Y is selected from the group consisting of Fe, Mn, Mg, Zn, Cu, Ni, Co, Mo, V, W, the alkali metals, the alkaline earth metals, polyatomic cations containing any of the foregoing (e.g., $VO^{+2}$), amines, and mixtures thereof; and $R_8$ and $R_9$ are individually and respectively selected from the group consisting of nothing (i.e., the groups are non-existent), $CH_2$, $C_2H_4$, and $C_3H_6$.

As can be appreciated, the Class II polymers typically have different types and sequences of repeat units. For example, a Class II polymer comprising B' and C' repeat units may include all three forms of B' repeat units and all three forms of C' repeat units. However, for reasons of cost and ease of synthesis, the most useful Class II polymers are made up of B' and C' repeat units. In the case of the Class II polymers made up principally of B' and C' repeat units, $R_5$, $R_6$, $R_{10}$, and $R_{11}$ are individually and respectively selected from the group consisting of H, the alkali metals, $NH_4$, and the $C_1$-$C_4$ alkyl ammonium groups. This particular Class II polymer is sometimes referred to as a butanedioic methylenesuccinic acid copolymer and can include various salts and derivatives thereof.

The Class II polymers may have a wide range of repeat unit concentrations in the polymer. For example, Class II polymers having varying ratios of B':C' (e.g., 10:90, 60:40, 50:50 and even 0:100) are contemplated and embraced by the present invention. Such polymers would be produced by varying monomer amounts in the reaction mixture from which the final product is eventually produced and the B' and C' type repeat units may be arranged in the polymer backbone in random order or in an alternating pattern.

The Class II polymers may have a wide variety of molecular weights, ranging for example from 500-5,000,000, depending chiefly upon the desired end use. Additionally, n can range from about 1-10,000 and more preferably from about 1-5,000.

Preferred Class II polymers are usually synthesized using dicarboxylic acid monomers, as well as precursors and derivatives thereof. For example, polymers containing mono and dicarboxylic acid repeat units with vinyl ester repeat units and vinyl alcohol repeat units are contemplated; however, polymers principally comprised of dicarboxylic acid repeat units are preferred (e.g., at least about 85%, and more preferably at least about 93%, of the repeat units are of this character). Class II polymers may be readily complexed with salt-forming cations using conventional methods and reactants.

Synthesis of the Class II Polymers

In general, the Class II polymers are made by free radical polymerization serving to convert selected monomers into the desired polymers with repeat units. Such polymers may be further modified to impart particular structures and/or properties. A variety of techniques can be used for generating free radicals, such as addition of peroxides, hydroperoxides, azo initiators, persulfates, percarbonates, per-acid, charge transfer complexes, irradiation (e.g., UV, electron beam, X-ray, gamma-radiation and other ionizing radiation types), and combinations of these techniques. Of course, an extensive variety of methods and techniques are well known in the art of polymer chemistry for initiating free-radical polymerizations. Those enumerated herein are but some of the more frequently used methods and techniques. Any suitable technique for performing free-radical polymerization is likely to be useful for the purposes of practicing the present invention.

The polymerization reactions are carried out in a compatible solvent system, namely a system which does not unduly interfere with the desired polymerization, using essentially any desired monomer concentrations. A number of suitable aqueous or non-aqueous solvent systems can be employed, such as ketones, alcohols, esters, ethers, aromatic solvents, water and mixtures thereof. Water alone and the lower ($C_1$-$C_4$) ketones and alcohols are especially preferred, and these may be mixed with water if desired. In some instances, the polymerization reactions are carried out with the substantial exclusion of oxygen, and most usually under an inert gas such as nitrogen or argon. There is no particular criticality in the type of equipment used in the synthesis of the polymers, i.e., stirred tank reactors, continuous stirred tank reactors, plug flow reactors, tube reactors and any combination of the foregoing arranged in series may be employed. A wide range of suitable reaction arrangements are well known to the art of polymerization.

In general, the initial polymerization step is carried out at a temperature of from about 0° C. to about 120° C. (more preferably from about 30° C. to about 95° C. for a period of from about 0.25 hours to about 24 hours and even more preferably from about 0.25 hours to about 5 hours). Usually, the reaction is carried out with continuous stirring.

After the polymerization reaction is complete, the Class II polymers may be converted

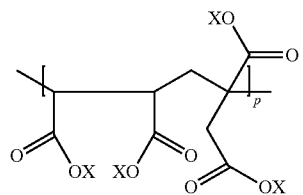

to partial or saturated salts using conventional techniques and reactants.

Preferred Class II Maleic-Itaconic Polymers

The most preferred Class II polymers are composed of maleic and itaconic B' and C' repeat units and have the generalized formula where X is either H or another salt-forming cation, depending upon the level of salt formation.

In a specific example of the synthesis of a maleic-itaconic Class II polymer, acetone (803 g), maleic anhydride (140 g), itaconic acid (185 g) and benzoyl peroxide (11 g) were stirred together under inert gas in a reactor. The reactor provided included a suitably sized cylindrical jacketed glass reactor with mechanical agitator, a contents temperature measurement device in contact with the contents of the reactor, an inert gas inlet, and a removable reflux condenser. This mixture was heated by circulating heated oil in the reactor jacket and stirred vigorously at an internal temperature of about 65-70° C. This reaction was carried out over a period of about 5 hours. At this point, the contents of the reaction vessel were poured into 300 g water with vigorous mixing. This gave a clear solution. The solution was subjected to distillation at reduced pressure to drive off excess solvent and water. After sufficient solvent and water have been removed, the solid product of the reaction precipitates from the concentrated solution, and is recovered. The solids are subsequently dried in vacuo. A schematic representation of this reaction is shown below.

Step 1

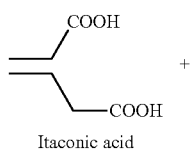

Itaconic acid

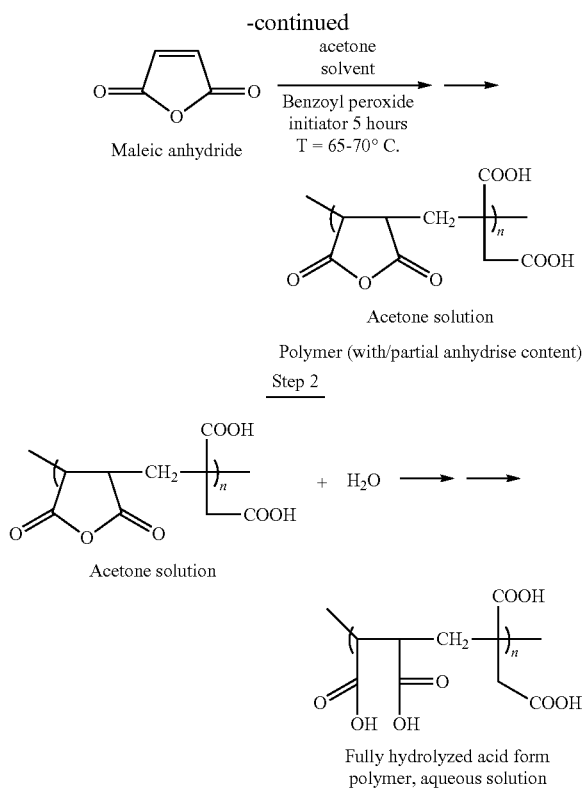

Preferred Uses of the Novel Polymers of the Invention

The novel (Class I) polymers of the invention, either alone, as a part of a mixed polymer product, and/or with other ingredients, can be used in a variety of contexts, some of which are described below. All of the previous disclosures relating to the Class I, IA, and II polymers is applicable to each of the uses described below, i.e., the entirety of the previous polymer disclosures should be considered as incorporated by reference into each of the following categories of use. Likewise, any definitions set forth in the categories of use are to be considered as applicable to all such categories.

1. Agricultural Actives

The Class I polymers hereof (with or without complexed ions) may be used directly as agricultural actives. For example, such polymers may be dispersed in a liquid aqueous medium and applied foliarly to plant leaves or applied to the earth adjacent growing plants. It has been found that the polymers increase the plant's uptake of both polymer-borne metal nutrients and ambient non-polymer nutrients found in adjacent soil. In such uses, effective amounts of compositions comprising the above-defined polymers are employed, either in liquid dispersions or in dried, granular form. Thus, application of polymer alone results in improved plant growth characteristics, presumably by increasing the availability of naturally occurring ambient nutrients. Typically, the polymers are applied at a level of from about 0.001 to about 100 lbs. polymer per acre of soil or growing plants, and more preferably from about 0.005 to about 50 lbs. polymer per acre, and still more preferably from about 0.01 to about 2 lbs.

2. Fertilizer Uses

In other preferred uses, the Class I polymers may be used to form composite products where the polymers are in intimate contact with fertilizer products including but not limited to phosphate-based fertilizers such as MAP, DAP, triple superphosphate, ordinary superphosphate, any one of a number of well known N—P—K fertilizer products, and/or fertilizers containing nitrogen materials such as ammonia (anhydrous or aqueous), ammonium nitrate, ammonium sulfate, urea, ammonium phosphates, sodium nitrate, calcium nitrate, potassium nitrate, nitrate of soda, urea formaldehyde, metal (e.g., zinc, iron) ammonium phosphates; phosphorous materials such as calcium phosphates (normal phosphate and super phosphate), ammonium phosphate, ammoniated super phosphate, phosphoric acid, superphosphoric acid, basic slag, rock phosphate, colloidal phosphate, bone phosphate; potassium materials such as potassium chloride, potassium sulfate, potassium nitrate, potassium phosphate, potassium hydroxide, potassium carbonate; calcium materials, such as calcium sulfate, calcium carbonate, calcium nitrate; magnesium materials, such as magnesium carbonate, magnesium oxide, magnesium sulfate, magnesium hydroxide; sulfur materials such as ammonium sulfate, sulfates of other fertilizers discussed herein, ammonium thiosulfate, elemental sulfur (either alone or included with or coated on other fertilizers); micronutrients such as Zn, Mn, Cu, Fe, B, Mo, and other micronutrients discussed herein; oxides, sulfates, chlorides, and chelates of such micronutrients (e.g., zinc oxide, zinc sulfate and zinc chloride); such chelates sequestered onto other carriers such as EDTA; boron materials such as boric acid, sodium borate or calcium borate; organic wastes and waste waters such as manure, sewage, food processing industry by-products, and pulp and paper mill by-products; and molybdenum materials such as sodium molybdate. As known in the art, these fertilizer products can exist as dry powders/granules or as water dispersions. The fertilizers may be of the conventional variety, or they may be starter fertilizers.

In such contexts, the Class I polymers may be mixed with the fertilizer products, applied as a surface coating to the fertilizer products, or otherwise thoroughly mixed with the fertilizer products. Preferably, in such combined fertilizer/polymer compositions, the fertilizer is in the form of particles having an average diameter of from about powder size (less than about 0.001 cm) to about 10 mm, more preferably from about 0.1 mm to about 5 mm, and still more preferably from about 0.15 mm to about 3 mm. The polymer is present in such combined products at a level of from about 0.01 g to about 7 g polymer per 100 g fertilizer (e.g., phosphate-based fertilizer), more preferably from about 0.08 g to about 5 g polymer per 100 g fertilizer, and still more preferably from about 0.09 g to about 2 g polymer per 100 g fertilizer. Again, the polymeric fraction of such combined products may include the polymers defined above, or such polymers complexed with the aforementioned ions. In the case of the combined fertilizer/polymer products, the combined product is applied at a level so that the amount of polymer applied is from about 10-150 g polymer per acre of soil, more preferably from about 30-125 g polymer per acre, and still more preferably from about 40-120 g polymer per acre of soil. The combined products can likewise be applied as liquid dispersions or as dry granulated products, at the discretion of the user. When polymers in accordance with the present invention are used as a coating, the polymer comprises between about 0.005% and about 15% by weight of the coated fertilizer product, more preferably the polymer comprises between about 0.01% and about 10% by weight of the coated fertilizer product, and most preferably between 0.5% and about 1% by weight of the coated fertilizer product. It has been found that polymer-coated fertilizer products obtain highly desirable characteristics due to the alteration of mechanical and physical properties of the fertilizer.

Especially preferred Class I polymers for use in agricultural contexts are synthesized as partial sodium salts and include the following repeat units: maleic—from about 20-55 mole percent, more preferably from about 25-50 mole percent, and most preferably from about 30-45 mole percent; itaconic—from about 35-65 mole percent, more preferably from about 40-60 mole percent, and most preferably about 50 mole percent; total sulfonated—from about 2-40 mole percent, more preferably from about 3-25 mole percent, and most preferably from about 5-20 mole percent. The total sulfonated fraction is preferably made up of a combination of methallylsulfonic and allylsulfonic repeat units, namely, methallylsulfonic—from about 1-20 mole percent, more preferably from about 3-15 mole percent, and most preferably from about 4-6 mole percent, and allylsulfonic—from about 0.1-10 mole percent, more preferably from about 0.5-8 mole percent, and most preferably from about 1-5 mole percent. These types of polymers are typically converted to partial or complete salts (preferably using cations such as alkali metal, ammonium, zinc, and mixtures thereof) at a pH of from about 0.2-4, more preferably from about 0.3-3, and most preferably from about 1-2.5.

As mentioned, these preferred agricultural-use Class I polymers are advantageously initially synthesized as partial sodium salts. This is due to the fact that the most preferred sulfonated repeat units are derived from the sodium salts, for reasons of cost and availability.

One preferred polymer of this type is a partial sodium salt having a pH of about 1, with a repeat unit molar composition of maleic 45 mole percent, itaconic 50 mole percent, methallylsulfonic 4 mole percent, and allylsulfonic 1 mole percent. This specific polymer is referred to herein as the "T5" polymer.

Useful variants of the T5 polymer include mixed sodium and zinc partial salts having about 5% w/w Zn on a metals basis and with a pH of about 3. It is made by reacting the T5 tetrapolymer with basic zinc carbonate in water. Alternately, the product may be made by reaction with zinc metal.

Another type of preferred polymer is a "T-20" tetrapolymer containing about 30 mole percent maleic repeat units, about 50 mole percent itaconic repeat units, and a total of about 20 mole percent sulfonated repeat units, made up of about 15 mole percent methallylsulfonate repeat units and about 5 mole percent allylsulfonate repeat units. Variants of T-20 tetrapolymers include partial salts (preferably alkali metal, ammonium, zinc, and mixtures thereof) having a pH of from about 1-3. One such variant is a partial mix sodium and ammonium salt at a pH of about 2.5, made by adding ammonia to the partial T-20 sodium salt aqueous solution until the target pH is achieved. This polymer has a significant lipophyllic character and is useful in pesticide-containing formulations.

Preferred formulations for coating granular nitrogenous fertilizers (e.g., urea) include a novel tetrapolymer of the invention (preferably T5 polymer), boric acid, low molecular weight polyvinyl alcohol, and water. For example, such coating formulations may have from about 20-50% w/w (most preferably about 34% w/w) tetrapolymer, from about 0.1-5% w/w (more preferably about 1.5% w/w) low molecular weight polyvinyl alcohol, and from about 25-60% w/w (most preferably about 57.5% w/w) water. Such formulations are compatible with colorant dyes and provide superior coating performance.

Preferred formulations for addition to liquid nitrogenous fertilizers include a novel tetrapolymer of the invention in the form of a mixed calcium/sodium salt (preferably T5 polymer), lactic acid, boric acid, and water at a pH of from about 0.5-3. For example, such formulations may have from about 20-50% w/w (most preferably about 35.5% w/w) tetrapolymer, from about 20-40% w/w (more preferably about 30% w/w) lactic acid, from about 2-10% w/w (more preferably about 4.5% w/w) and from about 20-45% w/w (most preferably about 30% w/w) water.

Example 5—Evaluation of Tetrapolymer Partial Salt as a Phosphorus Fertilizer Enhancer The above-described ammonium/sodium tetrapolymer Salt B was tested to determine its ability to prevent fixation of phosphorus in dispersions. In soils, the fixing of phosphorus (phosphates) with cations, such as Ca, Mn, Mg, Al, and Fe, limit phosphorus uptake by plants, which in turn depresses yields. This soil interaction can be simulated in water using water-soluble phosphates (P2O5) in dispersion. These dispersions create an ideal environment for fixation testing, with visible precipitation of phosphates being determined.

A first stock dispersion of 1000 ppm free calcium ion made from calcium chloride was prepared and aliquots thereof were pipetted into eight separate 50 mL Erlenmeyer flasks, followed by dilution with deionized water to 50 mL of total volume. This yielded two sets of flasks nos. 1 and 2, each set having four individual flasks respectively containing 10, 100, 500, and 1000 ppm of free calcium ion in water.

A second stock dispersion of 1000 ppm free iron ion made from ferrous sulfate was also created and pipetted into eight additional Erlenmeyer flasks to create two sets of flasks nos. 3 and 4, each set having four individual flasks respectively containing 10, 100, 500, and 1000 ppm of free iron ion in water.

The B tetrapolymer partial salt (a sodium/ammonium salt, pH about 2.5) was added to the flasks of sets 1 and 3 at a rate of 0.50% (v/v) to represent a typical liquid fertilizer usage rate. Sets 2 and 4 were left untreated as controls. A 1% by weight phosphate dispersion was made using standard 10-34-0 liquid phosphate fertilizer, and this was pipetted into all 16 of the Erlenmeyer flasks in a stepwise fraction, using 0.5 mL aliquots, up to a total of 5.0 mL phosphate dispersion. The extent of phosphate precipitation was recorded after each aliquot was added to the flasks, using a percentage scale where 0% was clear and colorless, and 100% was a solid opaque precipitate (lower concentrations of cations did not reach 100% and were completely bonded at a level of about 75% precipitate). The results of these tests are set forth in the following Tables 1 and 2.

TABLE 1

Example 5, - Ca Flasks, Sets 1 and 2

| Ca Reaction Flasks | Phosphate Addition - mL | | | | | | | | | |
|---|---|---|---|---|---|---|---|---|---|---|
| | 0.5 | 1.0 | 1.5 | 2.0 | 2.5 | 3.0 | 3.5 | 4.0 | 4.5 | 5.0 |
| 10 ppm | 0% | 0% | 0% | 0% | 0% | 0% | 0% | 0% | 0% | 0% |
| 10 ppm w/ Polymer | 0% | 0% | 0% | 0% | 0% | 0% | 0% | 0% | 0% | 0% |
| 100 ppm | 0% | 30% | 60% | 75% | 75% | 75% | 75% | 75% | 75% | 75% |
| 100 ppm w/ Polymer | 0% | 0% | 0% | 0% | 0% | 0% | 0% | 0% | 0% | 0% |
| 500 ppm | 10% | 40% | 70% | 100% | 100% | 100% | 100% | 100% | 100% | 100% |
| 500 ppm w/ Polymer | 0% | 0% | 0% | 0% | 0% | 20% | 30% | 50% | 100% | 100% |
| 1000 ppm | 30% | 60% | 100% | 100% | 100% | 100% | 100% | 100% | 100% | 100% |
| 1000 ppm w/ Polymer | 0% | 0% | 0% | 0% | 20% | 40% | 70% | 100% | 100% | 100% |

TABLE 2

Example 5, - Fe Flasks, Sets 3 and 4

| Fe Reaction Flasks | Phosphate Addition - mL | | | | | | | | | |
|---|---|---|---|---|---|---|---|---|---|---|
| | 0.5 | 1.0 | 1.5 | 2.0 | 2.5 | 3.0 | 3.5 | 4.0 | 4.5 | 5.0 |
| 10 ppm | 0% | 0% | 0% | 0% | 0% | 0% | 0% | 0% | 0% | 0% |
| 10 ppm w/ Polymer | 0% | 0% | 0% | 0% | 0% | 0% | 0% | 0% | 0% | 0% |
| 100 ppm | 0% | 0% | 0% | 0% | 0% | 0% | 0% | 0% | 0% | 0% |
| 100 ppm w/ Polymer | 0% | 0% | 0% | 0% | 0% | 0% | 0% | 0% | 0% | 0% |
| 500 ppm | 40% | 80% | 100% | 100% | 100% | 100% | 100% | 100% | 100% | 100% |
| 500 ppm w/ Polymer | 0% | 0% | 0% | 0% | 0% | 0% | 25% | 50% | 100% | 100% |
| 1000 ppm | 70% | 100% | 100% | 100% | 100% | 100% | 100% | 100% | 100% | 100% |
| 1000 ppm w/ Polymer | 0% | 0% | 0% | 0% | 0% | 20% | 40% | 80% | 100% | 100% |

As is evident from the foregoing data, the polymers of the invention significantly reduced precipitation in all of the Ca and Fe reaction flasks, save for the 10 ppm dispersions, which had no precipitation at any level of phosphate addition. In the Ca reaction flasks at 100 ppm, the polymer-supplemented flasks exhibited no precipitation at any level of phosphate addition, whereas the 100 ppm flask with no polymer exhibited significant precipitation (corresponding to prevention of phosphorus fixation) beginning at the 1.5 mL level. Similarly, in the Fe reaction flasks at 500 and 1000 ppm phosphate addition levels, the performance of the polymer-supplemented flasks was significantly better than the no-polymer flasks.

3. Uses with Sulfur-Bearing Compounds

One particularly important agricultural utility of the novel Class I polymers of the invention is the ability of the polymers to enhance the agricultural effectiveness of sulfur-bearing compounds such as gypsum, one or more members of the Kieserite Group, potassium magnesium sulfate, elemental sulfur, and mixtures thereof. The polymers may be applied as surface coatings as solid fertilizers, or may be added to solutionized liquid fertilizers as a liquid; this combined liquid material may then be sprayed on soils prior to planting. Moreover, the polymers liberate soluble calcium and soluble sulfur-containing species from gypsum and other minerals in compositions containing significant amounts of calcium sulfate. Calcium sulfate exists in a wide range of forms, crystal structures, hydration levels, and particle morphologies, but the calcium sulfate content thereof has been difficult to exploit for plant nutrition purposes, owing to the poor solubility of the calcium and sulfur-containing species therein.

It has been found that the addition of comparatively small levels of the novel polymers of the invention applied to solid calcium sulfate or calcium sulfate-containing materials serves to increase the liberation of calcium and soluble sulfur species from calcium sulfate or similar materials. Generally, the polymers are used at a level of from about 0.01-10% w/w, more preferably from about 0.05-2% w/w, where the total weight of the polymer/calcium sulfate or calcium sulfate-containing products is taken as 100% by weight.

Example 6—Class I Tetrapolymer Treatment of Gypsum

In this test, granulated gypsum was coated with the T5 polymer, which was diluted with water to give a polymer content of about 40% w/w. This polymeric material was applied to the gypsum at a rate of 0.50% w/w.

Three no-polymer gypsum controls were run for each test, along with three gypsum polymer-added replications. In each test, a 1 g sample of the uncoated or coated gypsum was placed in a 50 mL Erlenmeyer flask, followed by the addition of 10 mL of water and shaking on a reciprocating shaker at low setting for a selected period of time. After the selected shaking period, the content of each flask was filtered into a 50 mL centrifuge tube through Whatman 1 filter paper. Thereupon, the pH of the filtered solution was measured and the solution was then diluted 10 times with 2.0% nitric acid and analyzed via inductively coupled plasma Optical Emission Spectroscopy (ICP-OES) for sulfur and calcium content. The pH of the filtered solution was also recorded. The results are set forth in the following tables.

TABLE 1

Example 6

| 20 min. shake | % Ca | % S | pH | % Ca mean | % S mean |
|---|---|---|---|---|---|
| Control Samples | 1.55 | 1.69 | 6.96 | 1.81 | 2.04 |
| Rep. 2 | 2.17 | 2.43 | 6.7 | | |
| Rep. 3 | 1.72 | 2.00 | 6.58 | | |
| T5 Polymer Samples | 1.41 | 1.54 | 5.99 | 1.86 | 2.11 |
| Rep. 2 | 1.96 | 2.26 | 6.14 | | |
| Rep. 3 | 2.20 | 2.53 | 6.17 | | |

TABLE 2

Example 6,

| 60 min. shake | % Ca | % S | pH | % Ca mean | % S mean |
|---|---|---|---|---|---|
| Control Samples | 1.71 | 1.91 | 7.08 | 1.74 | 1.98 |
| Rep. 2 | 1.72 | 1.99 | 7.13 | | |
| Rep. 3 | 1.78 | 2.06 | 7.25 | | |
| T5 Polymer Samples | 1.46 | 1.61 | 6.00 | 1.87 | 2.12 |
| Rep. 2 | 1.86 | 2.12 | 6.05 | | |
| Rep. 3 | 2.31 | 2.64 | 6.48 | | |

TABLE 3

Example 6,

| 240 min. shake | % Ca | % S | pH | % Ca mean | % S mean |
|---|---|---|---|---|---|
| Control Samples | 1.72 | 1.93 | 6.94 | 1.81 | 2.10 |
| Rep. 2 | 1.93 | 2.24 | 7.32 | | |
| Rep. 3 | 1.77 | 2.12 | 7.23 | | |
| T5 Polymer Samples | 1.52 | 1.69 | 6.32 | 2.09 | 2.35 |
| Rep. 2 | 1.99 | 2.20 | 6.45 | | |
| Rep. 3 | 2.76 | 3.17 | 6.35 | | |

TABLE 4

Example 6,

| 24 hr. shake | % Ca | % S | pH | % Ca mean | % S mean |
|---|---|---|---|---|---|
| Control Samples | 1.88 | 2.14 | 7.24 | 1.82 | 2.10 |
| Rep. 2 | 1.84 | 2.10 | 7.21 | | |
| Rep. 3 | 1.73 | 2.07 | 7.24 | | |
| T5 Polymer Samples | 2.00 | 2.19 | 6.79 | 2.10 | 2.35 |
| Rep. 2 | 1.96 | 2.23 | 6.95 | | |
| Rep. 3 | 2.36 | 2.62 | 6.53 | | |

As can be seen, as the shake time increased, the amount of free sulfur and calcium increased significantly over the controls, confirming that the T5 polymer gypsum coating increased the amount of available sulfur for plant uptake.

Still further increased availability of sulfur and calcium can be obtained using a coating mixture comprising 35% w/w T5 tetrapolymer, about 2% w/w low molecular weight polyvinyl alcohol, and about 40% w/w glycolic acid, with the balance being water. By removing most of the water and adding glycolic acid and PVA, improved coating behaviors were noted, allowing smaller quantities of polymer to be used.

4. Uses with Liquid or Solutionized Fertilizers

Use of alpha-hydroxy carboxylic acid compounds with the polymers of the invention in the context of liquid or solutionized fertilizers can yield improved results. The alpha-hydroxy acids may be used singly or in mixtures of 2 or more acids. The most useful alpha-hydroxy acids are saturated and essentially free of double bonds and carbon ring structures, including both aliphatic and aromatic ring structures (i.e., no more than about 5 mole percent of double bonds or ring structures). Such alpha-hydroxy acids possess at least one carboxylic acid functional group and have at least one hydroxyl group on the carbon atom adjacent to the carboxylate group. Especially preferred acids of this character include lactic acid (D, L, or racemic mixtures are useful), glycolic acid, citric acid, tartaric acid, tartronic acid, glyceric acid, and dihydroxypropanedioic acid. The alpha-hydroxy acids may have more than one carboxylic acid functional group per molecule, more than one alphahydroxyl group, or any combination thereof. The preferred polymer/alpha-hydroxy acid formulations generally include from about 10-45% w/w, more preferably from about 15-35% w/w, of the polymers of the invention, which preferably includes at least one Class I polymer; from about 3-60% w/w, more preferably from about 10-40% w/w, of alpha-hydroxy carboxylic acid(s); and the balance being an inert solvent, preferably water. The foregoing ranges are based upon the total weight of the formulations taken as 100% by weight. The following representative formulation has been found to be particularly useful for use with liquid or solutionized fertilizers, especially solutionized gypsum: 35% w/w of the previously described T5 polymer, 30% w/w of glycolic acid, and with the balance being water.

The polymer/alpha-hydroxy carboxylic acid formulations may be further improved with the addition of polyvinyl alcohols (PVA's) thereto. While essentially all PVA's are useful, preferred PVA's are of relatively low average molecular weight, such that a 4% w/w solution of the PVA's in water at 20° C. ranges between about 1-1000 centipoise. Very small amounts of PVA's may be used in a range of from about 0.1% w/w-10% w/w of the total composition, and more preferably from about 0.05% w/w-2% w/w. It is also possible to use more than one molecular weight of PVA, but the PVA combinations advantageously are within the above viscosity ranges. Still further, preferred PVA's have high levels of hydrolysis, where at least 97 mole percent, and preferably at least about 98 mole percent, of the functional groups are hydrolyzed. A representative composition for use with gypsum includes 35% w/w of the T5 polymer, 30% w/w of glycolic acid, 1.5% w/w PVA (e.g., DuPont Elvanol 70-03), and the balance being water.

The pH levels of the liquid or solutionized fertilizers including the alpha-hydroxy acid formulations should be from about 0.5-3, more preferably about 1.

Example 7—Addition of Class I Tetrapolymer to UAN

In this series of tests, standard UAN was supplemented with 0.50% by weight of a mixture containing 35.5% by weight partial calcium salt of the T5 polymer (pH about 1.0), 4.5% by weight boric acid, 30% by weight lactic acid, with the balance being water. This material was used at a level of 40 gal/acre corresponding to 120 lbs of nitrogen/acre with different types of planted hybrid corn seeds. Comparative tests were also performed using no-polymer UAN, and UAN supplemented with the recommended label amount of commercially available Nutri Sphere-N for liquid fertilizers. All of the tests were done in 6 replications with the liquid fertilizers broadcast applied before emergence, two days after planting. Corn yields were recorded for each test and averaged.

TABLE 1

Example 7.

| UAN Treatment | Hybrid | Yield (Bu/acre) |
|---|---|---|
| None | CL2133 | 106.2 |
| +NutriSphere-N | | 121.6 |
| +T5 mixture | | 148.6 |
| None | INT9333 | 115.8 |
| +NutriSphere-N | | 137.6 |
| +T5 mixture | | 140.6 |
| None | P8210HR | 124.1 |
| +NutriSphere-N | | 129 |
| +T5 mixture | | 139.8 |
| None | DK30-23 | 91.9 |
| +NutriSphere-N | | 93.9 |
| +T5 mixture | | 139.7 |

5. Specific Uses with Potassium-Containing Granular Fertilizers

Another significant agricultural utility of the Class I polymers of the invention involves use with potassium-containing granular fertilizers in order to decrease fertilizer losses. That is, the polymers may be applied directly to at least partially water soluble granular potassium fertilizer, and especially potassium chloride-based fertilizers, at a level of from about 0.001-10% by weight, more preferably from about 0.004-2% by weight, based upon the total weight of the polymer/potassium fertilizer material taken as 100% by weight. In order to form suitable coatings on these fertilizers without generation of significant amounts of hydrochloric acid, it is generally preferred that the polymers be neutralized with a suitable cation to a pH of from about 0.1-4, and more preferably about 1. One preferred formulation involves creating a partial salt of the T5 polymer (at a concentration of 50% w/w) in aqueous dispersion at 20° C. by reacting the polymer with 45% w/w potassium hydroxide to reach a pH of about 0.1-4. The resulting dispersion is adjusted by evaporation and water addition to give a 40% w/w solids dispersion at room temperature. This composition, referred to as "T5-K—Na," is coated onto commercial potassium chloride granules at a level of from about 0.001% w/w-5% w/w.

It has been found that use of the novel polymers of the invention is not essential in formulations including soluble potassium-containing solids. Thus, this aspect of the invention contemplates provision of formulations comprising a mixture of a Class I and/or Class II polymer (having at least about 10%, more preferably at least about 25%, of the functional groups thereon being anionic) in partial or complete salt form, with substantially all of the cations therein being alkaline metal and at a pH between about 0.5-3, and more preferably about 1. Such formulations are applied to at least partially soluble potassium-containing solids and allowed to dry, so that the dried residue thereof is applied to the surface of the solids. The same levels of use described above with reference to the calcium sulfate products are applicable to these potassium products as well. The polymer is usually present at a level of from about 0.001-10% by weight, more preferably from about 0.004-2% by weight, based upon the total weight of the polymer/potassium-containing solids product taken as 100% by weight.

6. Uses as Seed Coatings

Another alternative use of the Class I polymers in accordance with the present invention includes using the polymers as seed coatings. In such cases, the polymers comprise at least about 0.001-10% by weight of the coated seed, more preferably from about 0.004-2% by weight of the coated seed. Use of the polymer as a seed coating provides polymer in close proximity to the seed when planted so that the polymer can exert its beneficial effects in the environment where it is most needed. That is, the new polymers provide an environment conducive to enhanced plant growth in the area where the effects can be localized around the desired plant. In the case of seeds, the polymer coating provides an enhanced opportunity for seed germination, subsequent plant growth, and an increase in plant nutrient availability, which is provided by the polymer salts.

In preferred practice, the Class I polymers are in aqueous dispersion and have a relatively high metals content, and particularly micronutrient metals, such as Zn, Mn, B, Fe, Mo, and Cu, to provide sufficient micronutrients for optimum seed growth. Moreover, the polymers are desirably solutions relatively free of suspended or settled solids for reasons of homogeneity and cosmetic appearance, and should have a pH in the range of from about 2-8, and preferably from about 5-7. In practice, the polymers are applied to the surfaces of seeds in any convenient fashion, and allowed to dry thereon, so that the finished seeds have the dried residue of the original liquid polymer and nutrients on the surfaces thereof.

7. Uses in Reducing Atmospheric Ammonia

The novel Class I polymers hereof may be used to treat livestock or poultry confinement facilities in order to reduce and mitigate the effects of gaseous ammonia within the facility. Generally, such facilities have a manure collection zone, upright walls forming an enclosure, and a roof substantially covering the zone. This utility involves applying a treatment material to the manure within the collection zone in an amount effective to lower the concentration of gaseous ammonia within the facility. Such material comprises an aqueous mixture of a polymer in accordance with the present invention, and particularly an amine, alkali metal or alkaline earth (e.g., calcium or ammonium) partial or saturated salt of the polymer. Preferably, the treating mixture is applied directly into the collection zone (e.g., manure pit) below the enclosure. The treating material including the polymer hereof should be applied at a level of from about 0.005-3 gallons per ton of manure, and more preferably from about 0.01-2.5 gallons per ton. The composition is preferably acidic having a pH of from about 1-5, and more preferably from about 2-4. The treating material is operable to reduce the amount of gaseous ammonia within the confinement zone within 24 hours after application of the materials.

U.S. Patent Publication 2014/0041431 is incorporated by reference herein in its entirety. This publication describes techniques for reducing atmospheric ammonia through use of Class II polymers. These same techniques without alteration can be used with the Class I polymers of this invention, and also all different mixtures of Class I, Class IA, and Class II polymers.

It is sometimes useful to employ a plurality of different polymers in the treating compositions. For example, useful compositions may include from about 40-80% (more preferably 55-75%) by weight of a partial calcium salt of a Class I polymer of the invention, and from about 20-60% (more preferably 25-45%) by weight of a partial ammonium salt of the same or different polymer in accordance with the invention. Both of these polymers are in the form of 40% w/w aqueous dispersions, so that the total amount of polymer per se in each is 40% of the above-recited ranges.

The polymers of the invention (i.e., Class I polymers, or different mixtures of Class I, Class IA, and Class II polymers) may also be used, alone or in combination with other polymers, to treat areas subject to ammonia gas evolution, e.g., household pet litters, in order to reduce the ammonia odor emanating therefrom.

The complete treatment materials should preferably contain at least about 30-60% by weight (more preferably from about 35-50% by weight) polymer solids derived from all of the polymers present in the treatment materials, and from about 40-70% by weight (more preferably from about 50-65% by weight) water. Other ingredients may be used apart from the polymers and water, such as pH adjustment agents, buffering agents, preservatives, and emulsifiers. Any such other ingredients are preferably used at a minor level, e.g., from about 1-10% by weight. The pH of the complete treating materials should be acidic, preferably from about 1-5, more preferably from about 2-4.

When the preferred treating materials comprise calcium and ammonium partial salts of the polymers, it is desirable that the amount of the calcium partial salt polymer is greater than the amount of the ammonium partial salt polymer, on a weight basis. That is, taking the total weight of both polymer salt solids as 100% by weight, the calcium partial salt copolymer solids should be present at a level of from about 50-80% by weight (more preferably from about 55-75% by weight, and most preferably from about 60-65% by weight), and the ammonium partial salt copolymer solids should be present at a level of from about 20-50% by weight (more preferably from about 25-45% by weight, and most preferably from about 35-40% by weight).

Application of the dual partial salt copolymer materials of the invention is quite straightforward. In the case of manure collection pits, the material need only be poured onto the top of the manure and will quite readily spread and diffuse throughout the mass of the manure to promptly reduce the amount of gaseous nitrogen generated and maintained within the confinement facility. In the case of dairy or poultry barns having floor structures with litter and manure atop or mixed with the litter, the treating material is advantageously sprayed onto the top of the litter-manure mixture, with or without mixing. Here again, the action of the treating material is quite prompt and long-lasting.

Generally, the treating mixtures are used at a level of from about 0.005-3 gallons of the material per ton of manure, more preferably from about 0.01-2.5 gallons/ton, still more preferably from about 0.02-1 gallon per ton, and most preferably from about 0.03-0.035 gallon per ton.

Almost immediately upon application of the treating material to the manure, the amount of gaseous ammonia within the confinement facility is perceptibly lowered, and such reduction persists for a considerable time. Generally, the prevailing amount of gaseous ammonia should be reduced by at least about 50% (more preferably at least about 60%) within 24 hours after application. A single treatment also preferably serves to maintain at least about a 30% gaseous ammonia reduction (more preferably at least about 40%) for at least about 14 days (more preferably at least about 21 days).

8. Uses as Animal Feed and/or Water Amendments

U.S. patent application Ser. No. 14/049,887, filed Oct. 9, 2013, discloses the use of Class I and/or Class II polymers as animal feed or water amendments serving to lower ammonia concentrations in the animal's excrement. That application is incorporated by reference herein in its entirety. The methods, animal feeds, and animal waters disclosed therein can be directly duplicated, without any alternations, in the context of the present invention save for the use of any mixture of Class I, Class IA, and Class II polymers hereof. Thus, the types of polymer salts, the range of polymer solids, and the amounts of water remain the same in the present invention. Likewise, the same specific methods of use may be employed in the context of the present invention, with the only difference being the particular polymers utilized.

For example, conventional poultry feeds comprising feed ingredients including quantities of corn and soybean meal can be improved using the amendments containing Class I polymers alone or in combination with other polymers, such as the Class IA and Class II polymers. In like manner, poultry water may be supplemented in the same fashion. In either instance, the amount of amendment used should be sufficient to reduce volatilized ammonia derived from the feces of poultry, as compared with poultry receiving the same feed and/or water, but without the amendments. Similarly, mammalian animal feeds and waters can be improved by the addition of the copolymers of the invention, again in amounts sufficient to reduce volatilized ammonia derived from mammalian excrement, as compared with animals receiving the same feed and/or water, but without the amendments.

The complete amendments should preferably contain at least about 30-60% by weight of total copolymer solids (more preferably from about 35-50% by weight solids), and from about 40-70% by weight water (most preferably from about 50-65% water). However, the amendments may also include other ingredients apart from the two partial salt copolymers and water, such as pH adjustment agents, buffering agents, preservatives, and emulsifiers. Any such other ingredients are preferably used at a minor level, e.g., from about 1-10% by weight. The pH of the complete amendments should be acid, preferably from about 1-5, more preferably from about 2-4.

A preferred amendment comprises an aqueous mixture including a partial calcium salt of a Class I copolymer and a partial ammonium salt of a Class I copolymer, the calcium partial salt copolymer solids should be present in an amount greater than the amount of the ammonium partial salt copolymer solids therein. That is, taking the total weight of both copolymer salt solids as 100% by weight, the calcium partial salt copolymer solids should be present at a level of from about 50-80% by weight (more preferably from about 55-75% by weight, and most preferably from about 60-65% by weight), and the ammonium partial salt copolymer solids should be present at a level of from about 20-50% by weight (more preferably from about 25-45% by weight, and most preferably from about 35-40% by weight). Also, the individual copolymer salts in water should both have a pH on the order of from about 1-4.

Generally speaking, the amendments of the invention are administered to animals by adding the amendments to otherwise conventional animal feeds, and/or adding the amendments to the animal water supply, or both.

In the case of poultry, use can be made of commercially available or custom poultry feeds, which are typically substantially dry and particulate in nature. Such feeds typically contain yellow corn at a level of from about 45-65% by weight, together with soybean at a level of from about 18-45% by weight. These feeds also commonly include a variety of other ingredients, such as meat and bone meals, fats, salt, limestone or oyster shell, amino acids, vitamins and minerals, and have analyses of protein (N×6.25) of from about 15-32%, and a Metabolizable Energy (ME) value of from about 1100-1600 kcal/lb. Further information about conventional poultry feeds can be found in Poultry Nutrition and Feeding, Section 12, *Animal Nutrition Handbook*, pp. 316-331 (2009), which is wholly incorporated herein by reference. The amendments of the invention, typically in aqueous liquid form, are sprayed or otherwise applied to the dry poultry feed ingredients with mixing, to substantially intersperse the copolymer materials with the feed ingredients. The improved feed is then fed ad libitum to poultry. The complete water/copolymer salt amendments should be present in an improved feed at a level of from about 0.05-0.25% by weight (more preferably from about 0.1-0.2% by weight), where the total weight of the supplemented or amended feed is taken as 100% by weight. This corresponds to a level of from about 0.015-0.15% by weight (more preferably 0.03-0.12% by weight) of copolymer solids per se in the poultry feed.

In the case of adding the complete water/copolymer salt amendments to poultry water, the usage would typically be at a level of from about 0.01-0.25% by volume, more preferably from about 0.05-0.2% by volume, where the total amount of supplemented or amended water is taken as 100% by volume. This corresponds to a level of from about 0.003-0.15% by volume (more preferably 0.0045-0.12% by volume) of the copolymer solids per se in the poultry water. Inasmuch as the preferred partial salt copolymers of the invention and the MTM® product, are water soluble, the complete amendments readily mix and evenly disperse in the poultry water.

The amendments of the invention, used either with poultry feed or poultry water can be fed to virtually any poultry, e.g., chicken, duck, goose, peafowl, swan, ostrich, pigeon, turkey, guineafowl, pheasant, rhea, and emu.

Where the complete amendments are employed to supplement mammalian animal feeds and/or waters, the same general techniques and amounts of complete amendments and copolymers are employed. For example, the amendments may be directly mixed with animal feeds or used as a top dressing thereon. Likewise, the animals' water supply is supplemented as described previously. The fact that the copolymers are water soluble greater facilitates uses thereof. The amendments of the invention may be fed to a wide variety of livestock, e.g., mammals such as cattle, sheep, swine, and horses.

As indicated above, it is preferred that the amendments of the invention be used in the form of aqueous mixtures containing copolymer salt(s). However, and especially in the case of amendments to poultry or animal waters, the copolymer solids can be added as is, and not in a complete water/copolymer amendment. In such instances, the above ranges of addition of the copolymers themselves are applicable.

9. Pesticide Adjuvants

The Class I polymers of the invention can be used to enhance the effectiveness of a wide spectrum of pesticides. As used herein, "pesticide" refers to any agent with pesticidal activity (e.g., herbicides, insecticides, fungicides, and nematocides) and is preferably selected from the group consisting of insecticides, herbicides, and mixtures thereof, but normally excluding materials which assertedly have a plant-fertilizing effect, for example, sodium borate and zinc compounds such as zinc oxide, zinc sulfate, and zinc chloride. The well known pyrethroid and organophosphate pesticides are suitable for use in the invention, as well as glyphosate and glufosinate herbicides.

In some cases, the polymer, which may be in the free acid, partial, or full salt form, is in aqueous dispersion and has a pH of from about 1-10, more preferably from about 2-7, and most preferably from 2-4, 7, and 8-9; the pH is often determined by the type of pesticide employed, inasmuch as some may be unstable in low pH ranges, while others break down at higher pH ranges. The polymers may be blended with the pesticide to form a mixture which then can be applied to soil, in foliar applications, onto hard surfaces, as aerosols, as additives to liquid or solid compositions (e.g., manure), or in any other context where pesticidal activity is desired. Alternately, the pesticide and polymer may be simultaneously or sequentially (typically within 24 hours of each other) applied to soil. Where mixed compositions are employed, they are typically in the form of aqueous dispersions, generally having water, pesticide, and polymer fractions. Other minor ingredients may also be used in the compositions such as surfactants and pH adjustment agents, or any of the other aforementioned adjuvants or additives known in the art. Compositions comprising a polymer of the invention and micronutrients have also proven to be very effective, with micronutrients selected from the group consisting of Mn, Zn, Cu, Ni, Co, Mo, V, Cr, Fe, and B, with a combination of Mn, Zn, and Cu being particularly preferred. Micronutrient-supplemented polymers can be used with glyphosate, to avoid the characteristic blocking reactions between glyphosate and micronutrients.

The amount of polymer in the pesticide compositions of the invention can vary over wide limits, and the principal consideration is one of polymer cost. Generally, the polymer should be present at a level of from about 0.05-10% by weight (more preferably from about 0.1-4% by weight, and most preferably from about 0.2-2% by weight) based upon the total weight of the pesticide composition taken as 100% by weight.

The pesticides used in the compositions of the invention are broadly selected from insecticides and herbicides. In the context of insecticides, synthetic pyrethroids and organophosphates are particularly preferred. For example, permethrin (C21H20Cl2O3, (3-phenoxyphenyl) methyl 3-(2,2-dichloroethenyl)-2,2-dimethyl-cyclopropane-1-carboxylate, CAS#52645-53-1) and bifenthrin (C23H22ClF3O2, (2-methyl-3-phenylphenyl) methyl (1S,3S)-3-[(Z)-2-chloro-3,3,3-trifluoroprop-1-enyl]-2,2-dimethylcyclopropane-1-carboxylate, CAS#82657-04-3) are suitable pyrethroids. A typical organophosphate pesticide useful in the invention is malathion (C10H19O6PS2, 2-(dimethoxyphosphinothioyl-thio) butanedioic acid diethyl ester, CAS#121-75-5).

More generally, the following insecticides are useful in the invention:
antibiotic insecticides: allosamidin, thuringiensin
    macrocyclic lactone insecticides
        avermectin insecticides: abamectin, doramectin, emamectin, eprinomectin, ivermectin, selamectin
        milbemycin insecticides: lepimectin, ilbemectin, milbemycin oxime, moxidectin
    spinosyn insecticides: spinetoram, spinosad
arsenical insecticides: calcium arsenate, copper acetoarsenite, copper arsenate, lead arsenate, potassium arsenite, sodium arsenite
botanical insecticides: anabasine, azadirachtin, d-limonene, nicotine, pyrethrins (cinerins (cinerin I, cinerin II), jasmolin I, jasmolin II, pyrethrin I, pyrethrin II), quassia, rotenone, ryania, sabadilla
carbamate insecticides: bendiocarb, carbaryl
    benzofuranyl methylcarbamate insecticides: benfuracarb, carbofuran, carbosulfan, decarbofuran, furathiocarb
    dimethylcarbamate insecticides: dimetan, dimetilan, hyquincarb, pirimicarb
    oxime carbamate insecticides: alanycarb, aldicarb, aldoxycarb, butocarboxim, butoxycarboxim, methomyl, nitrilacarb, oxamyl, tazimcarb, thiocarboxime, thiodicarb, thiofanox phenyl methylcarbamate insecticides: allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC, xylylcarb desiccant insecticides: boric acid, diatomaceous earth, silica gel diamide insecticides: chlorantraniliprole, cyantraniliprole, flubendiamide dinitrophenol insecticides: dinex, dinoprop, dinosam, DNOC fluorine insecticides: barium hexafluorosilicate, cryolite, sodium fluoride, sodium hexafluorosilicate, sulfluramid formamidine insecticides: amitraz, chlordimeform, formetanate, formparanate fumigant insecticides: acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride, tetrachloroethane inorganic insecticides: borax, boric acid, calcium polysulfide, copper oleate, diatomaceous earth, mercurous chloride, potassium thiocyanate, silica gel, sodium thiocyanate, see also arsenical insecticides, see also fluorine insecticides insect growth regulators
    chitin synthesis inhibitors: bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, triflumuron
    juvenile hormone mimics: epofenonane, fenoxycarb, hydroprene, kinoprene, methoprene, pyriproxyfen, triprene
    juvenile hormones: juvenile hormone I, juvenile hormone II, juvenile hormone III
    moulting hormone agonists: chromafenozide, halofenozide, methoxyfenozide, tebufenozide
    moulting hormones: a-ecdysone, ecdysterone
    moulting inhibitors: diofenolan
    precocenes: precocene I, precocene II, precocene III
    unclassified insect growth regulators: dicyclanil nereistoxin analogue insecticides: bensultap, cartap, thiocyclam, thiosultap nicotinoid insecticides: flonicamid
    nitroguanidine insecticides: clothianidin, dinotefuran, imidacloprid, thiamethoxam
    nitromethylene insecticides: nitenpyram, nithiazine
    pyridylmethylamine insecticides: acetamiprid, imidacloprid, nitenpyram, thiacloprid organochlorine insecticides: bromo-DDT, camphechlor, DDT (pp'-DDT), ethyl-DDD, HCH (gamma-HCH, lindane), methoxychlor, pentachlorophenol, TDE
    cyclodiene insecticides: aldrin, bromocyclen, chlorbicyclen, chlordane, chlordecone, dieldrin, dilor, endosulfan (alpha-endosulfan), endrin, HEOD, heptachlor, HHDN, isobenzan, isodrin, kelevan, mirex organophosphorus insecticides
    organophosphate insecticides: bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP, tetrachlorvinphos
    organothiophosphate insecticides: dioxabenzofos, fosmethilan, phenthoate
    aliphatic organothiophosphate insecticides: acethion, amiton, cadusafos, chlorethoxyfos, chlormephos, demephion (demephion-O, demephion-S), demeton (demeton-O, demeton-S), demeton-methyl (demeton-O-methyl, demeton-S-methyl), demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos, thiometon
    aliphatic amide organothiophosphate insecticides: amidithion, cyanthoate, dimethoate, ethoatemethyl, formothion, mecarbam, omethoate, prothoate, sophamide, vamidothion
    oxime organothiophosphate insecticides: chlorphoxim, phoxim, phoxim-methyl
    heterocyclic organothiophosphate insecticides: azamethiphos, coumaphos, coumithoate, dioxathion, endothion, menazon, morphothion, phosalone, pyraclofos, pyridaphenthion, quinothion
    benzothiopyran organothiophosphate insecticides: dithicrofos, thicrofos
    benzotriazine organothiophosphate insecticides: azinphos-ethyl, azinphos-methyl
    isoindole organothiophosphate insecticides: dialifos, phosmet
    isoxazole organothiophosphate insecticides: isoxathion, zolaprofos
    pyrazolopyrimidine organothiophosphate insecticides: chlorprazophos, pyrazophos
    pyridine organothiophosphate insecticides: chlorpyrifos, chlorpyrifos-methyl
    pyrimidine organothiophosphate insecticides: butathiofos, diazinon, etrimfos, lirimfos, pirimiphos-ethyl, pirimiphos-methyl, primidophos, pyrimitate, tebupirimfos
    quinoxaline organothiophosphate insecticides: quinalphos, quinalphos-methyl
    thiadiazole organothiophosphate insecticides: athidathion, lythidathion, methidathion, prothidathion
    triazole organothiophosphate insecticides: isazofos, triazophos
    phenyl organothiophosphate insecticides: azothoate, bromophos, bromophos-ethyl, carbophenothion, chlorthiophos, cyanophos, cythioate, dicapthon, dichlofenthion, etaphos, famphur, fenchlorphos, fenitrothion, fensulfothion, fenthion, fenthion-ethyl, heterophos, j odfenphos, mesulfenfos, parathion, parathion-methyl, phenkapton, phosnichlor, profenofos, prothiofos, sulprofos, temephos, trichlormetaphos-3, trifenofos
    phosphonate insecticides: butonate, trichlorfon
    phosphonothioate insecticides: mecarphon
    phenyl ethylphosphonothioate insecticides: fonofos, trichloronat
    phenyl phenylphosphonothioate insecticides: cyanofenphos, EPN, leptophos
    phosphoramidate insecticides: crufomate, fenamiphos, fosthietan, mephosfolan, phosfolan, pirimetaphos
    phosphoramidothioate insecticides: acephate, isocarbophos, isofenphos, isofenphos-methyl, methamidophos, propetamphos
    phosphorodiamide insecticides: dimefox, mazidox, mipafox, schradan oxadiazine insecticides: indoxacarb
oxadiazolone insecticides: metoxadiazone
phthalimide insecticides: dialifos, phosmet, tetramethrin pyrazole insecticides: chlorantraniliprole, cyantraniliprole, dimetilan, tebufenpyrad, tolfenpyrad
  phenylpyrazole insecticides: acetoprole, ethiprole, fipronil, pyraclofos, pyrafluprole, pyriprole, vaniliprole
pyrethroid insecticides
pyrethroid ester insecticides: acrinathrin, allethrin (bioallethrin), barthrin, bifenthrin, bioethanomethrin, cyclethrin, cycloprothrin, cyfluthrin (beta-cyfluthrin), cyhalothrin, (gamma-cyhalothrin, lambda-cyhalothrin), cypermethrin (alpha-cypermethrin, beta-cypermethrin, theta-cypermethrin, zeta-cypermethrin), cyphenothrin, deltamethrin, dimefluthrin, dimethrin, empenthrin, fenfluthrin, fenpirithrin, fenpropathrin, fenvalerate (esfenvalerate), flucythrinate, fluvalinate (tau-fluvalinate), furethrin, imiprothrin, metofluthrin, permethrin (biopermethrin, transpermethrin), phenothrin, prallethrin, profluthrin, pyresmethrin, resmethrin (bioresmethrin, cismethrin), tefluthrin, terallethrin, tetramethrin, tralomethrin, transfluthrin
pyrethroid ether insecticides: etofenprox, flufenprox, halfenprox, protrifenbute, silafluofen
pyrimidinamine insecticides: flufenerim, pyrimidifen
pyrrole insecticides: chlorfenapyr
tetramic acid insecticides: spirotetramat
tetronic acid insecticides: spiromesifen
thiazole insecticides: clothianidin, thiamethoxam
thiazolidine insecticides: tazimcarb, thiacloprid
thiourea insecticides: diafenthiuron
urea insecticides: flucofuron, sulcofuron, see also chitin synthesis inhibitors
unclassified insecticides: closantel, copper naphthenate, crotamiton, EXD, fenazaflor, fenoxacrim, hydramethylnon, isoprothiolane, malonoben, metaflumizone, nifluridide, plifenate, pyridaben, pyridalyl, pyrifluquinazon, rafoxanide, sulfoxaflor, triarathene, triazamate.

The foregoing insecticides, and links for a further identification and description of the insecticides, can be found at http://www.alanwood.net/pesticides/class_insecticides.html, which is incorporated herein in its entirety.

A particularly preferred herbicide is glyphosate (C3H8NO5P, [(phosphonomethyl) amino] acetic acid, CAS#1071-83-6). Other herbicides which can be used in the invention include:
amide herbicides: allidochlor, amicarbazone, beflubutamid, benzadox, benzipram, bromobutide, cafenstrole, CDEA, cyprazole, dimethenamid (dimethenamid-P), diphenamid, epronaz, etnipromid, fentrazamide, flucarbazone, flupoxam, fomesafen, halosafen, isocarbamid, isoxaben, napropamide, naptalam, pethoxamid, propyzamide, quinonamid, saflufenacil, tebutam
  anilide herbicides: chloranocryl, cisanilide, clomeprop, cypromid, diflufenican, etobenzanid, fenasulam, flufenacet, flufenican, ipfencarbazone, mefenacet, mefluidide, metamifop, monalide, naproanilide, pentanochlor, picolinafen, propanil, sulfentrazone
    arylalanine herbicides: benzoylprop, flamprop (flamprop-M),
    chloroacetanilide herbicides: acetochlor, alachlor, butachlor, butenachlor, delachlor, diethatyl, dimethachlor, metazachlor, metolachlor (S-metolachlor), pretilachlor, propachlor, propisochlor, prynachlor, terbuchlor, thenylchlor, xylachlor
    sulfonanilide herbicides: benzofluor, cloransulam, diclosulam, florasulam, flumetsulam, metosulam, perfluidone, pyrimisulfan, profluazol
  sulfonamide herbicides: asulam, carbasulam, fenasulam, oryzalin, penoxsulam, pyroxsulam, see also sulfonylurea herbicides
  thioamide herbicides: bencarbazone, chlorthiamid
antibiotic herbicides: bilanafos
aromatic acid herbicides:
  benzoic acid herbicides: chloramben, dicamba, 2,3,6-TBA, tricamba
    pyrimidinyloxybenzoic acid herbicides: bispyribac, pyriminobac
    pyrimidinylthiobenzoic acid herbicides: pyrithiobac
  phthalic acid herbicides: chlorthal
  picolinic acid herbicides: aminopyralid, clopyralid, picloram
  quinolinecarboxylic acid herbicides: quinclorac, quinmerac
arsenical herbicides: cacodylic acid, CMA, DSMA, hexaflurate, MAA, MAMA, MSMA, potassium arsenite, sodium arsenite
benzoylcyclohexanedione herbicides: mesotrione, sulcotrione, tefuryltrione, tembotrione
benzofuranyl alkylsulfonate herbicides: benfuresate, ethofumesate
benzothiazole herbicides: benazolin, benzthiazuron, fenthiaprop, mefenacet, methabenzthiazuron
carbamate herbicides: asulam, carboxazole, chlorprocarb, dichlormate, fenasulam, karbutilate, terbucarb
carbanilate herbicides: barban, BCPC, carbasulam, carbetamide, CEPC, chlorbufam, chlorpropham, CPPC, desmedipham, phenisopham, phenmedipham, phenmediphamethyl, propham, swep
cyclohexene oxime herbicides: alloxydim, butroxydim, clethodim, cloproxydim, cycloxydim, profoxydim, sethoxydim, tepraloxydim, tralkoxydim
cyclopropylisoxazole herbicides: isoxachlortole, isoxaflutole
dicarboximide herbicides: cinidon-ethyl, flumezin, flumiclorac, flumioxazin, flumipropyn, see also uracil herbicides
dinitroaniline herbicides: benfluralin, butralin, dinitramine, ethalfluralin, fluchloralin, isopropalin, methalpropalin, nitralin, oryzalin, pendimethalin, prodiamine, profluralin, trifluralin
dinitrophenol herbicides: dinofenate, dinoprop, dinosam, dinoseb, dinoterb, DNOC, etinofen, medinoterb
diphenyl ether herbicides: ethoxyfen
  nitrophenyl ether herbicides: acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen, oxyfluorfen
dithiocarbamate herbicides: dazomet, metam
halogenated aliphatic herbicides: alorac, chloropon, dalapon, flupropanate, hexachloroacetone, iodomethane, methyl bromide, monochloroacetic acid, SMA, TCA
imidazolinone herbicides: imazamethabenz, imazamox, imazapic, imazapyr, imazaquin, imazethapyr
inorganic herbicides: ammonium sulfamate, borax, calcium chlorate, copper sulfate, ferrous sulfate, potassium azide, potassium cyanate, sodium azide, sodium chlorate, sulfuric acid
nitrile herbicides: bromobonil, bromoxynil, chloroxynil, dichlobenil, iodobonil, ioxynil, pyraclonil
organophosphorus herbicides: amiprofos-methyl, anilofos, bensulide, bilanafos, butamifos, 2,4-DEP, DMPA, EBEP, fosamine, glufosinate (glufosinate-P), glyphosate, piperophos oxadiazolone herbicides: dimefuron, methazole, oxadiargyl, oxadiazon oxazole herbicides: carboxazole, fenoxasulfone, isouron, isoxaben, isoxachlortole, isoxaflutole, monisouron, pyroxasulfone, topramezone phenoxy herbicides: bromofenoxim, clomeprop, 2,4-DEB, 2,4-DEP, difenopenten, disul, erbon, etnipromid, fenteracol, trifopsime phenoxyacetic herbicides: 4-CPA, 2,4-D, 3,4-DA, MCPA, MCPA-thioethyl, 2,4,5-T phenoxybutyric herbicides: 4-CPB, 2,4-DB, 3,4-DB, MCPB, 2,4,5-TB phenoxypropionic herbicides: cloprop, 4-CPP, dichlorprop (dichlorprop-P), 3,4-DP, fenoprop, mecoprop, (mecoprop-P)

aryloxyphenoxypropionic herbicides: chlorazifop, clodinafop, clofop, cyhalofop, diclofop, fenoxaprop, (fenoxaprop-P), fenthiaprop, fluazifop, (fluazifop-P), haloxyfop, (haloxyfop-P), isoxapyrifop, metamifop, propaquizafop, quizalofop, (quizalofop-P), trifop phenylenediamine herbicides: dinitramine, prodiamine pyrazole herbicides: azimsulfuron, difenzoquat, halosulfuron, metazachlor, metazosulfuron, pyrazosulfuron, pyroxasulfone benzoylpyrazole herbicides: benzofenap, pyrasulfotole, pyrazolynate, pyrazoxyfen, topramezone phenylpyrazole herbicides: fluazolate, nipyraclofen, pinoxaden, pyraflufen pyridazine herbicides: credazine, pyridafol, pyridate pyridazinone herbicides: brompyrazon, chloridazon, dimidazon, flufenpyr, metflurazon, norflurazon, oxapyrazon, pydanon pyridine herbicides: aminopyralid, cliodinate, clopyralid, diflufenican, dithiopyr, flufenican, fluroxypyr, haloxydine, picloram, picolinafen, pyriclor, pyroxsulam, thiazopyr, triclopyr pyrimidinediamine herbicides: iprymidam, tioclorim quaternary ammonium herbicides: cyperquat, diethamquat, difenzoquat, diquat, morfamquat, paraquat thiocarbamate herbicides: butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate, vernolate thiocarbonate herbicides: dimexano, EXD, proxan thiourea herbicides: methiuron triazine herbicides: dipropetryn, indaziflam, triaziflam, trihydroxytriazine chlorotriazine herbicides: atrazine, chlorazine, cyanazine, cyprazine, eglinazine, ipazine, mesoprazine, procyazine, proglinazine, propazine, sebuthylazine, simazine, terbuthylazine, trietazine methoxytriazine herbicides: atraton, methometon, prometon, secbumeton, simeton, terbumeton methylthiotriazine herbicides: ametryn, aziprotryne, cyanatryn, desmetryn, dimethametryn, methoprotryne, prometryn, simetryn, terbutryn triazinone herbicides: ametridione, amibuzin, hexazinone, isomethiozin, metamitron, metribuzin triazole herbicides: amitrole, cafenstrole, epronaz, flupoxam triazolone herbicides: amicarbazone, bencarbazone, carfentrazone, flucarbazone, ipfencarbazone, propoxycarbazone, sulfentrazone, thiencarbazone triazolopyrimidine herbicides: cloransulam, diclosulam, florasulam, flumetsulam, metosulam, penoxsulam, pyroxsulam uracil herbicides: benzfendizone, bromacil, butafenacil, flupropacil, isocil, lenacil, saflufenacil, terbacil urea herbicides: benzthiazuron, cumyluron, cycluron, dichloralurea, diflufenzopyr, isonoruron, isouron, methabenzthiazuron, monisouron, noruron phenylurea herbicides: anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron, thidiazuron sulfonylurea herbicides:

pyrimidinylsulfonylurea herbicides: amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, nicosulfuron, orthosulfamuron, oxasulfuron, primisulfuron, propyrisulfuron, pyrazosulfuron, rimsulfuron, sulfometuron, sulfosulfuron, trifloxysulfuron triazinylsulfonylurea herbicides: chlorsulfuron, cinosulfuron, ethametsulfuron, iodosulfuron, metsulfuron, prosulfuron, thifensulfuron, triasulfuron, tribenuron, triflusulfuron, tritosulfuron thiadiazolylurea herbicides: buthiuron, ethidimuron, tebuthiuron, thiazafluron, thidiazuron unclassified herbicides: acrolein, allyl alcohol, aminocyclopyrachlor, azafenidin, bentazone, benzobicyclon, bicyclopyrone, buthidazole, calcium cyanamide, cambendichlor, chlorfenac, chlorfenprop, chlorflurazole, chlorflurenol, cinmethylin, clomazone, CPMF, cresol, cyanamide, ortho-dichlorobenzene, dimepiperate, endothal, fluoromidine, fluridone, flurochloridone, flurtamone, fluthiacet, indanofan, methyl isothiocyanate, OCH, oxaziclomefone, pentachlorophenol, pentoxazone, phenylmercury acetate, prosulfalin, pyribenzoxim, pyriftalid, quinoclamine, rhodethanil, sulglycapin, thidiazimin, tridiphane, trimeturon, tripropindan, tritac.

The foregoing herbicides, and links for a further identification and description of the herbicides, can be found at http://www.alanwood.net/pesticides/class_herbicides.html, which is incorporated herein in its entirety.

The following are the most preferred insecticides for use in the invention: botanical, carbamate, diamide, fumigant, insect growth regulators, nicotinoid, organochlorine, organophosphorus, phthalimide, pyrazole, pyrethroid, pyrethroid ester, pyrethroid ether, pyrimidinamine, pyrrole, thiazole, thiazolidine, and thiourea.

The following are the most preferred herbicides for use in the invention: amide, aromatic acid, benzothiazole, carbamate, carbanilate, cyclohexene oxime, dicarboximide, dinitroaniline, dinitrophenol, diphenyl ether, imidazolinone, organophosphorus, oxadiazolone, oxazole, phenoxy, phenylenediamine, pyrazole, pyridine, pyridazinone, quaternary ammonium, thiocarbamate, thiocarbonate, thiourea, triazine, triazinone, triazole, triazolone, triazolopyrimidine, urea, and unclassified.

The following are the most preferred fungicides for use in the invention: Dithiocarbamates, Nitrial, Benzimidazoles, Dicarboximides, Sterol Inhibitors (SI)/Demethylase Inhibitors (DMI), Carboxamides/Anilides, Strobilurins, Phenylpyrrole, Phynylamide, Aromic Hydrocarbin, Polyoxin, Pyridinamine, Cyanoimidazole, Carbamate, and Phosphonate.

Example 8—Evaluation of Tetrapolymer Partial Salt as Pesticide Adjuvant

In this test, the effectiveness of the previously described ammonium/sodium tetrapolymer partial salt B as a glyphosate adjuvant was compared with an aqueous mixture containing 40% by weight of a maleic-itaconic polymer ammonium partial salt, having equimolar amounts of maleic and itaconic moieties, and a pH of about 2 (referred to herein as "M-I ammonium partial salt").

Glyphosate test dispersion treatments were prepared as follows, using 50 mL of glyphosate dispersion in each treatment:

Treatment A—glyphosate alone

Treatment B—glyphosate+1.0% (v/v) MSO

Treatment C—glyphosate+0.50% (v/v) M-I ammonium partial salt+1.0% (v/v) MSO

Treatment D—glyphosate+0.50% (v/v) tetrapolymer salt B+1.0% (v/v) MSO

Treatment E—glyphosate+0.50% (v/v) CS

Treatment F—glyphosate+0.50% (v/v) M-I ammonium partial salt+0.50% (v/v) CS

Treatment G—glyphosate+0.50% (v/v) tetrapolymer salt B+0.50% (v/v) CS

Treatment H—glyphosate+0.50% (v/v) tetrapolymer salt B

The glyphosate used in all of the formulations was an isopropylamine glyphosate sold under the designation "Glyphosate Star Gold," and was prepared as an aqueous dispersion in a 50 mL tube, using the conventional commercial concentration, namely 32 oz of glyphosate per acre. The other ingredients were mixed with the glyphosate to complete the Treatments. The added materials were M-I ammonium partial salt, methylated seed oil surfactant (MSO), and ChemSurf 90 (CS). The latter product is a commercially available aqueous surfactant containing 90% alkylarylpolyoxykane ether, isopropanol and free fatty acids, and is manufactured by Chemorse, Ltd. of Des Moines, Iowa.

Twenty-four 6.75 inch soil pots were planted with pre-germinated pods containing two Waterhemp (*Amaranthus rudis*) plants known to be resistant to glyphosate herbicides. Plants were allowed to reach between 10 and 15 cm in height, whereupon they were sprayed with the above Treatments using a hand-held CO2 pressurized cone-nozzle sprayer calibrated to deliver 0.230 mL of Treatment to each pot, which is equivalent to a ten-gallon tank mixture sprayed over one acre.

A numerical scale based upon live plant observations was used to gauge the effectiveness of each Treatment, with 0.0 being no effect and 5.0 being completely effective. Three replicate observations were made on day 6 and day 12 after spraying, with the cumulative means of all replications representing the effectiveness of the corresponding Treatment. The results of this series of tests is set forth in Tables 3 and 4 below.

TABLE 1

Example 8, - Day 6 Observations

| Group ID | Rep 1 | Rep 2 | Rep 3 | Mean |
|---|---|---|---|---|
| Treatment A | 3.0 | 4.0 | 0.0 | 2.3 |
| Treatment B | 5.0 | 4.0 | 0.5 | 3.2 |
| Treatment C | 3.0 | 3.0 | 0.5 | 2.2 |
| Treatment D | 4.0 | 4.0 | 4.0 | 4.0 |
| Treatment E | 5.0 | 3.0 | 3.0 | 3.7 |
| Treatment F | 4.5 | 5.0 | 5.0 | 4.8 |
| Treatment G | 5.0 | 1.0 | 3.0 | 3.0 |
| Treatment H | 5.0 | 4.0 | 2.5 | 3.8 |

TABLE 2

Example 8, - Day 12 Observations

| Group ID | Rep 1 | Rep 2 | Rep 3 | Mean |
|---|---|---|---|---|
| Treatment A | 3.0 | 3.5 | 0 | 2.2 |
| Treatment B | 5.0 | 5.0 | 0.5 | 3.5 |
| Treatment C | 5.0 | 2.5 | 0 | 2.5 |
| Treatment D | 3.5 | 3.0 | 5.0 | 3.8 |
| Treatment E | 5.0 | 3.0 | 5.0 | 4.3 |
| Treatment F | 5.0 | 5.0 | 5.0 | 5.0 |
| Treatment G | 5.0 | 2.5 | 3.0 | 3.5 |
| Treatment H | 5.0 | 5.0 | 2.5 | 4.2 |

As illustrated in the foregoing data, the tetrapolymer products of the invention provided increase adjuvant activity in almost all instances, as compared with the no-polymer and M-I ammonium partial salt tests. This result was especially evident with Treatments D and F, where observations starting on Day 1 presented easily discernible differences between Treatments with and without the tetrapolymer additive.

Example 9—Class I Tetrapolymers as Herbicide Adjuvants

Glufosinate Trial

In this series of tests, commercially available Liberty glufosinate herbicide obtained from Bayer CropScience was supplemented with a T5 partial sodium and ammonium salt polymer (pH 2.5) at two different rates.

Tank mixtures were first made by mixing together 10 gallons of deionized water and Liberty herbicide at a rate equal to 29 ounces per acre. The polymer was then added at a rate of 0.50% v/v or 1% v/v immediately before spray application.

The liquid herbicide mixtures were targeted at 12-inch tall Waterhemp (*Amaranthus rudis*) having known resistance to glyphosate and triazine herbicides. All treatments were applied at 10 gal/acre using a teejet 8002 EVS nozzle in a DeVries Research Sprayer, at a rate of 29 fl. oz. per acre of Liberty herbicide. After 15 days, the percent by weight of remaining biomass for each plant was measured. The control (no polymer) exhibited 45% remaining biomass, whereas the 0.5% tetrapolymer test gave 20% remaining biomass, and the 1% tetrapolymer test gave 10% remaining biomass.

Dicamba Trial

In this series of tests, commercially available Clarity Dicamba herbicide obtained from BASF Corporation was supplemented with a T5 partial sodium salt polymer (pH 8.0) at two different rates.

Tank mixtures were first made by mixing together 10 gallons of deionized water and Clarity herbicide at a rate equal to 16 ounces per acre. The polymer was then added at a rate of 0.50% v/v or 1% v/v immediately before spray application.

The liquid herbicide mixtures were targeted at Marestail (*Conyza canadensis*) at full rosette stage having known resistance to glyphosate herbicides. All treatments were applied at 10 gal/acre using a teejet 8002 EVS nozzle in a DeVries Research Sprayer, at a rate of 16 fl. oz. per acre of Clarity herbicide. After 7 days, the percent by weight of remaining biomass for each plant was measured. The control (no polymer) exhibited 65% remaining biomass, whereas the 0.5% tetrapolymer test gave 45% remaining biomass, and the 1% tetrapolymer test gave 50% remaining biomass. After 14 days, the control had 20% remaining biomass, the 0.5% tetrapolymer test gave 5% remaining biomass, and the 1% tetrapolymer test gave 15% remaining biomass.

2,4-D Trial

In this series of tests, commercially available 2,4-D diethylamine salt herbicide was supplemented with a T5 partial sodium and ammonium salt polymer (pH 2.5) at two different rates.

Tank mixtures were first made by mixing together 10 gallons of deionized water and 2,4-D herbicide at a rate equal to 32 ounces per acre. The polymer was then added at a rate of 0.50% v/v or 1% v/v immediately before spray application.

The liquid herbicide mixtures were targeted at Marestail (*Conyza canadensis*) at full rosette stage having known resistance to glyphosate herbicides. All treatments were applied at 10 gal/acre using a teejet 8002 EVS nozzle in a DeVries Research Sprayer, at a rate of 32 fl. oz. per acre of herbicide. After 7 days, the percent by weight of remaining biomass for each plant was measured. The control (no polymer) exhibited 70% remaining biomass, whereas the 0.5% tetrapolymer test gave 60% remaining biomass, and the 1% tetrapolymer test gave 65% remaining biomass. After 14 days, the control had 25% remaining biomass, the 0.5% tetrapolymer test gave 10% remaining biomass, and the 1% tetrapolymer test gave 15% remaining biomass.

10. Nitrification/Urease/Phosphate Fixation Inhibition

The Class I polymers of the invention have also been found to serve as useful inhibitors for the nitrification processes within soil, and to also inhibit phosphate fixation and urease activities therein. In this fashion, increased crop yields are realized owing to the fact that naturally occurring and fertilizer-supplied nitrogen and phosphate sources are more efficiently utilized by plants. The polymers of the invention may be applied directly to soil in aqueous dispersion or solid form and in amounts effective for controlling nitrification, urease activity, and phosphate fixation; more commonly, however, the polymers are used in conjunction with solid ammoniacal fertilizer (e.g., urea), or with fluid fertilizers (e.g., gaseous fertilizers or liquid UAN) containing ammoniacal nitrogen.

As used herein, "ammoniacal nitrogen" is a broad term embracing fertilizer compositions containing ammoniacal nitrogen ($NH_4$) as well as fertilizer compositions and other compounds which are precursors of ammoniacal nitrogen or that cause ammoniacal nitrogen to be generated when the fertilizers or compounds undergo various reactions such as hydrolysis. To give but one example, the polymers of the invention may be applied to or mixed with urea or other nitrogen-containing fertilizers which have no ammoniacal nitrogen therein as such. Nonetheless, such fertilizers will undergo reactions in the soil to generate ammoniacal nitrogen in situ. Thus, in this example urea or other precursor nitrogen-containing fertilizers would be deemed to contain ammoniacal nitrogen.

When the Class I polymers are used in the form of aqueous dispersions in intimate contact with or dispersed in ammoniacal nitrogen fertilizers, the polymer/fertilizer mixture is typically applied to soil adjacent growing plants or pre-applied to soils subject to nitrification. Aqueous polymer mixtures are typically used with liquid and dry fertilizers at relatively low levels up to about 2% by volume (e.g., 0.01-2% by volume) based upon the total volume of the liquid fertilizer material taken as 100% by volume. In such uses, it is also preferred that the pH levels should be up to about 3, more preferably up to about 2, and most preferably up to about 1. Moreover, such aqueous dispersions advantageously contain from about 10-85% by weight solids, more preferably from about 30-65% by weight solids, and most preferably about 40% by weight solids.

In preparing the polymer/liquid fertilizer materials of the invention, the ammoniacal nitrogen-containing fertilizer material(s) are suspended in water and the aqueous polymer mixture(s) are added thereto with mixing. No particular mixing regime or temperature conditions are required. Surprisingly, it has been found that these liquid fertilizer materials are quite stable and resist settling out or precipitation of solids over extended storage periods of at least about two weeks.

In the case of solid ammoniacal fertilizers, the polymers are directly applied to the fertilizer, typically at a level of from about 0.01-10% by weight, more preferably from about 0.05-2% by weight, based upon the total weight of the polymer/fertilizer product taken as 100% by weight. Normally, aqueous dispersions of the polymer are sprayed onto the solid fertilizers and allowed to dry, so that the polymeric dried residue remains on the surfaces of the fertilizers Example 10—Evaluation of Tetrapolymer Partial Salt as Urease Inhibitor—Method 1

Studies have shown that urea-containing fertilizers can lose up to 30% or more of their N if not incorporated into soil within 72 hours by tillage or rainfall. Volatilization occurs when urea hydrolyzes, i.e., it reacts with soil moisture and breaks down. The enzyme urease, which is produced by soil microorganisms, facilitates volatilization. Therefore, best management practices dictate that urease be inhibited to the extent possible.

In this test, the urease inhibition effectiveness of the tetrapolymers of the invention was determined, as compared with prior art maleic-itaconic partial salts. In the test, 50 mL Erlenmeyer flasks were charged with 25 mL of 1.0% (w/w) stock urea dispersion, and two levels of tetrapolymer salt B, namely 0.033% (v/v) (8.25 μL) and 0.066% (v/v) (16.5 μL). Comparative flasks were also prepared containing the same amounts of urea dispersion, but with a 40% solids aqueous dispersion of a partial calcium salt of a maleic-itaconic polymer containing equimolar amounts of maleic and itaconic moieties, and having a pH of from about 2.25-2.75, nominally 2.5 (referred to herein as "M-I Ca 2.5") and a 40% solids aqueous dispersion of a partial calcium salt of a maleic-itaconic polymer containing equimolar amounts of maleic and itaconic moieties, and having a pH of from about 1-2, nominally 1.5 (referred to herein as "M-I Ca 1.5"). Control flasks containing no urease inhibition polymer were also prepared.

A pH meter and electrode were used to record initial pH levels, whereupon an additional 1.0% (v/v) of urease enzyme dispersion was added to each flask. pH measurements were taken at timed intervals to track the breakdown of urea in the flasks. As the urea breaks down, ammonia ions are generated, causing a subsequent rise in the pH of the dispersions. By observing the rate of pH elevation, the effectiveness of urease inhibition can be measured.

TABLE 1

Example 10, - Trial 1: Urease Inhibition with 0.033% Inhibitor

| Polymer Salt | Salt B | M-I Ca 2.5 | M-I Ca 1.5 | Control |
|---|---|---|---|---|
| Initial pH | 4.122 | 4.084 | 3.088 | 7.000 |
| 30 Second pH | 8.400 | 4.818 | 3.362 | 9.295 (immediate) |

TABLE 1-continued

Example 10, - Trial 1: Urease Inhibition with 0.033% Inhibitor

| Polymer Salt | Salt B | M-I Ca 2.5 | M-I Ca 1.5 | Control |
|---|---|---|---|---|
| 120 Second pH | 9.105 | 8.389 | 3.753 | |
| 600 Second pH | x | x | 6.484 | |
| Increase (600 s) | 4.983 | 4.305 | 3.396 | |

TABLE 2

Example 10, - Trial 1: Urease Inhibition with 0.066% Inhibitor

| Polymer Salt | Salt B | M-I Ca 2.5 | M-I Ca 1.5 | Control |
|---|---|---|---|---|
| Initial pH | 3.943 | 3.908 | 3.496 | 7.000 |
| 30 Second pH | 4.087 | 4.055 | 3.559 | 9.295 (immediate) |
| 120 Second pH | 4.601 | 4.345 | 3.801 | |
| 600 Second pH | 9.305 | 6.504 | 4.636 | |
| Increase (600 s) | 5.362 | 2.596 | 1.14 | |

As illustrated, the control flasks without any polymeric urease inhibitor exhibited an immediate pH spike. However, the tetrapolymer salts of the invention gave functional urease inhibition results as compared with the prior art M-I Ca 2.5 and M-I Ca 1.5 products, particularly at the higher usage rate of Table 6.

Example 11—Evaluation of Tetrapolymer Partial Salt as Urease Inhibitor—Method 2

In this test, the urease inhibition properties of the tetrapolymers of the invention were determined as compared with the prior art M-I Ca 2.5 and M-I Ca 1.5 products, using a different technique. In particular, nine 50 mL Erlenmeyer flasks were charged with 25 mL each of deionized water, to give three flask sets A, B, and C, each set containing three flasks. Thereupon, 0.033% (v/v) of the M-I Ca 2.5, M-I Ca 1.5, and salt B polymers were individually added to the three flasks of each set. After the pH levels of the flasks containing water and polymer stabilized, 1% (v/v) urease dispersion was added to each of the nine flasks, and the individual flasks containing water/polymer/urease were allowed to incubate for three different time periods, namely 1 (set A), 3 (set B), and 10 (set C) minutes. The pH levels were taken at this point, followed by adding 0.5 mL of 50% (w/w) urea-water dispersion to each flask to obtain a total of 1% (w/w) of urea in each flask dispersion. pH measurements were then observed at time intervals of 30 seconds, 120 seconds, and 600 seconds. As the urea broke down in each flask, ammonia was released, causing a rise in pH in the dispersions. By observing the rate of pH rise, the effectiveness of urease inhibition was measured; this rate is directly affected by the amount of incubation time between the three sets.

TABLE 1

Example 11, - One Minute Incubation of Polymer/Urease - Set A

| Polymer | Salt B | M-I Ca 2.5 | M-I Ca 1.5 |
|---|---|---|---|
| Initial pH, H2O and polymer | 3.974 | 3.856 | 3.588 |
| H2O, Polymer, and Urease after one minute | 3.895 | 3.789 | 3.523 |
| 30 s after adding urea dispersion | 4.194 | 4.003 | 3.695 |
| 120 seconds | 4.510 | 4.353 | 3.763 |
| 600 seconds | 7.934 | 8.907 | 6.176 |

TABLE 2

Example 11, - Three Minute Incubation of Polymer/Urease - Set B

| Polymer | Salt B | M-I Ca 2.5 | M-I Ca 1.5 |
|---|---|---|---|
| Initial pH, H2O and polymer | 3.925 | 3.951 | 3.619 |
| H2O, Polymer, and Urease after one minute | 4.025 | 3.845 | 3.559 |
| 30 s after adding urea dispersion | 4.025 | 3.975 | 3.690 |
| 120 seconds | 4.260 | 4.043 | 3.761 |
| 600 seconds | 4.765 | 7.663 | 3.934 |

TABLE 3

Example 11, - Ten Minute Incubation of Polymer/Urease - Set C

| Polymer | Salt B | M-I Ca 2.5 | M-I Ca 1.5 |
|---|---|---|---|
| Initial pH, H2O and polymer | 3.987 | 3.832 | |
| H2O, Polymer, and Urease after one minute | 3.908 | 3.756 | |
| 30 s after adding urea dispersion | 4.049 | 3.848 | |
| 120 seconds | 4.081 | 3.879 | |
| 600 seconds | 4.140 | 3.951 | |

Example 12—Class I Polymer as Urease Enzyme Inhibitor

In a first series of tests, 25 mL aliquots of 1% (w/w) stock urea solution were combined in 50 mL Erlenmeyer flasks with four different test formulations at equal levels of 0.666% (v/v). A pH meter and electrode were used to record initial pH levels, and then 1.0% (v/v) urease solution was added to each flask. pH measurements over time (at 30 seconds, 120 seconds, and 600 seconds) were observed as a measure of urea breakdown, generating ammonia and consequently causing a rise in pH levels. The rates of pH rise were a measure of the effectiveness of urease inhibition. Two replications A and B were carried out for each test formulation.

The test formulations were:

No. 1—no polymer, 4% w/w boric acid, 30% w/w lactic acid, balance water, with added dye.

No. 2—T5 polymer as a mixed sodium/calcium partial salt in water, pH about 1.

No. 3—34% w/w T5 polymer as a mixed calcium/sodium partial salt, 4% w/w boric acid, 1.5% w/w low molecular weight polyvinyl alcohol, 22% w/w lactic acid, no dye, with the balance being water, pH of about 1.

No. 4—T5 polymer as a mixed sodium/calcium partial salt in water, pH about 1, with 4.3% w/w boric acid, and 32% w/w lactic acid.

The results of this first series of tests are set forth below.

TABLE 1

Example 12.

| Test Formulation | Replication | Initial pH | 30 s pH | 120 s pH | 600 s pH |
|---|---|---|---|---|---|
| 1 | A | 3.31 | 4.40 | 8.99 | 9.08 |
| 1 | B | 3.37 | 4.04 | 8.99 | 9.14 |
| 2 | A | 3.43 | 3.30 | 3.37 | 3.64 |
| 2 | B | 3.36 | 3.27 | 3.33 | 3.73 |
| 3 | A | 3.09 | 3.03 | 3.08 | 3.21 |
| 3 | B | 3.25 | 3.18 | 3.22 | 3.23 |
| 4 | A | 3.16 | 3.12 | 3.10 | 3.10 |
| 4 | B | 3.21 | 3.20 | 3.21 | 3.44 |

As illustrated in the foregoing data, test formulations containing Class I tetrapolymers without boric acid both gave sustained disablement of urease enzyme. Further testing has confirmed that the Class I tetrapolymers inhibit urease completely through 10 minutes.

In a second series of tests, the same formulation Nos. 1-4 were tested under a different procedure. Specifically, 24.5 mL of water was combined with the test formulations in 50 mL Erlenmeyer flasks to obtain a test formulation level of 0.033% v/v. Immediately thereafter, urease enzyme was added to each flask at a rate of 1.0% v/v, and allowed to incubate for 60 seconds or 300 seconds. Once the incubations were complete, initial pH measurements were taken and 0.5 mL of 50% w/w urea solution was added to each flask to bring the total solutions to 1% w/w of urea and water. Thereafter, pH measurements were taken at 60 seconds/300 seconds, 90 seconds/330 seconds, 180 seconds/400 seconds, and 600 seconds/900 seconds. Furthermore, ambient air ammonia concentrations from the respective flasks were measured after 4 hours as another indicator of urease inhibition. The results of this test are set forth below.

TABLE 2

Example 12.

| Test Formulation | Incubation Period/ Initial pH | Wait Time/pH | Wait Time/pH | Wait Time/pH | NH3/4 hours |
|---|---|---|---|---|---|
| 1 | 60 s/3.93 | 90 s/8.99 | 180 s/9.25 | 660 s/9.29 | 290 ppm |
| 1 | 300 s/4.05 | 330 s/9.04 | 420 s/9.14 | 900 s/9.22 | 220 ppm |
| 2 | 60 s/4.72 | 90 s/6.26 | 180 s/7.67 | 660 s/8.95 | 9 ppm |
| 2 | 300 s/4.34 | 330 s/6.71 | 420 s/8.11 | 900 s/8.84 | 9 ppm |
| 3 | 60 s/3.97 | 90 s/5.74 | 180 s/8.40 | 660 s/9.09 | 20 ppm |
| 3 | 300 s/4.14 | 330 s/5.90 | 420 s/6.36 | 900 s/7.08 | 9 ppm |
| 4 | 60 s/3.85 | 90 s/4.94 | 180 s/7.97 | 660 s/9.06 | 24 ppm |
| 4 | 300 s/3.88 | 330 s/5.28 | 420 s/6.94 | 900 s/8.50 | 9 ppm |

Example 13—Class I Tetrapolymers as Phosphorous Fixation Inhibitors

Phosphorous fertilizer can become tied-up or fixed with antagonistic cations in soils, which results in 75-95% of applied phosphorous becoming unavailable for plant uptake. It has been found that the Class I polymers of the invention are capable of reducing such phosphorous fixation by sequestration of antagonistic cations in the microenvironments of phosphorous fertilizers.

In a field test, two rates of phosphorous as diammonium phosphate (DAP) were broadcast-applied as a pre-plant fertilizer to a cotton field, namely 65 lbs of DAP per acre and 130 lbs of DAP per acre. The tests were two replications each of an unfertilized control, a DAP-only control, and DAP mixed with 0.25% w/w of a Class I polymer formulation. The formulation included 40% w/w of a partial zinc/sodium salt of T5 polymer, 5% w/w zinc, and the balance water, pH about 3.

Tissue tests were taken prior to first bloom from each plot, and the percent of phosphorous in the plant tissue was measured. After harvesting, lint yields were measured. The tissue phosphorous test results are set forth below in Table 1, whereas the yield tests are given in Table 2.

TABLE 1

Example 13.

| Treatment | % by weight Phosphorous in Tissue |
|---|---|
| unfertilized control | 0.21 |
| 65 lbs DAP | 0.41 |
| 65 lbs DAP w/ polymer | 0.5 |
| unfertilized control | 0.21 |
| 130 lbs DAP | 0.41 |
| 130 lbs DAP w/ polymer | 0.51 |

TABLE 2

Example 13.

| Treatment | Lint Yield lbs/acre |
|---|---|
| unfertilized control | 390 |
| 65 lbs DAP | 712 |
| 65 lbs DAP w/ polymer | 896 |
| unfertilized control | 390 |
| 130 lbs DAP | 781 |
| 130 lbs DAP w/ polymer | 900 |

These results confirm that the use of the Class I tetrapolymer with zinc gave a significant increase in tissue phosphorous levels and yields.

The foregoing Examples 5-13 illustrate specific uses of the novel Class I polymers of the invention in various contexts. It is to be understood that these Examples are provided by way of illustration only, and nothing therein should be taken as a limitation upon the overall scope of the invention.

We claim:

1. An anionic tetrapolymer comprising four repeat units randomly distributed along a length of a polymer chain,
    said repeat units being randomly located along the tetrapolymer,
    said tetrapolymer comprising 30-50 mole percent repeat units derived from maleic acid, 20-55 mole percent repeat units derived from itaconic acid, 1-25 mole percent repeat units derived from methallylsulfonic acid, and 1-20 mole percent repeat units derived from allylsulfonic acid, where the total amount of all of the repeat units in the tetrapolymer is taken as 100 mole percent.

2. An anionic polymer comprising at least four repeat units randomly distributed along a length of a polymer chain, said at least four repeat units including at least one each of type B, type C, and type G repeat units,
    said type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein the salts have salt-forming cations selected from the group consisting of metals, amines, and mixtures thereof, said type C repeat units selected from the group consisting of repeat units derived from monomers of itaconic acid, itaconic anhydride, and any isomers, esters, and the partial or complete salts of any of the foregoing, and mixtures of any of the foregoing, wherein the salts have salt-forming cations selected from the group consisting of metals, amines, and mixtures thereof, said type G repeat units selected from the group consisting of repeat units derived from substituted or unsubstituted sulfonated monomers possessing at least one carbon-carbon double bond and at least one sulfonate group, and any isomers, and the partial or complete salts of any of the foregoing, and mixtures of any of the foregoing, wherein the salts of the type G repeat units have salt-forming cations selected from the group consisting of metals, amines, and mixtures thereof, and wherein no more than about 5 mole percent of said type G repeat units have amide groups, and no more than about 5 mole percent of said type G repeat units have aromatic rings, at least about 90 mole percent of the repeat units therein are selected from the group consisting of type B, C, and G repeat units, and mixtures thereof, said repeat units being randomly located along the polymer, said polymer having no more than about 5 mole percent of each of (i) non-carboxylate olefin groups, (ii) ether repeat units, (iii) ester repeat units, (iv) non-sulfonated monocarboxylic repeat units, and (v) amide-containing repeat units, said polymer comprising about 25-50 mole percent repeat units derived from maleic acid and/or anhydride, about 40-60 mole percent repeat units derived from itaconic acid and/or anhydride, about 3-15 mole percent repeat units derived from methyallylsulfonic acid, and about 0.5-8 mole percent repeat units derived from allylsulfonic acid, where the total amount of all of the repeat units in the polymer is taken as 100 mole percent.

3. The polymer of claim 2, said polymer comprising about 30-45 mole percent repeat units derived from maleic acid and/or anhydride, about 40-55 mole percent repeat units derived from itaconic acid and/or anhydride, about 4-6 mole percent repeat units derived from methyallylsulfonic acid, and about 1-5 mole percent repeat units derived from allylsulfonic acid, where the total amount of all of the repeat units in the polymer is taken as 100 mole percent.

4. The polymer of claim 3, said polymer comprising 45 mole percent repeat units derived from maleic acid and/or anhydride, 50 mole percent repeat units derived from itaconic acid and/or anhydride, 4 mole percent repeat units derived from methyallylsulfonic acid, and 1 mole percent repeat units derived from allylsulfonic acid, where the total amount of all of the repeat units in the polymer is taken as 100 mole percent.

5. The polymer of claim 2, said polymer comprising about 30 mole percent repeat units derived from maleic acid and/or anhydride, about 50 mole percent repeat units derived from itaconic acid and/or anhydride, about 15 mole percent repeat units derived from methyallylsulfonic acid, and about 5 mole percent repeat units derived from allylsulfonic acid, where the total amount of all of the repeat units in the polymer is taken as 100 mole percent.

6. An anionic polymer comprising at least four repeat units randomly distributed along a length of a polymer chain, said at least four repeat units including at least one each of type B, type C, and type G repeat units, said type B repeat units selected from the group consisting of repeat units derived from substituted and unsubstituted monomers of maleic acid and/or anhydride, fumaric acid and/or anhydride, mesaconic acid and/or anhydride, mixtures of the foregoing, and any isomers, esters, acid chlorides, and partial or complete salts of any of the foregoing, wherein the salts have salt-forming cations selected from the group consisting of metals, amines, and mixtures thereof, said type C repeat units selected from the group consisting of repeat units derived from monomers of itaconic acid, itaconic anhydride, and any isomers, esters, and the partial or complete salts of any of the foregoing, and mixtures of any of the foregoing, wherein the salts have salt-forming cations selected from the group consisting of metals, amines, and mixtures thereof, said type G repeat units selected from the group consisting of repeat units derived from substituted or unsubstituted sulfonated monomers possessing at least one carbon-carbon double bond and at least one sulfonate group, and any isomers, and the partial or complete salts of any of the foregoing, and mixtures of any of the foregoing, wherein the salts of the type G repeat units have salt-forming cations selected from the group consisting of metals, amines, and mixtures thereof, and wherein no more than about 5 mole percent of said type G repeat units have amide groups, and no more than about 5 mole percent of said type G repeat units have aromatic rings, at least about 90 mole percent of the repeat units therein are selected from the group consisting of type B, C, and G repeat units, and mixtures thereof, said repeat units being randomly located along the polymer, said polymer having no more than about 5 mole percent of each of (i) non-carboxylate olefin groups, (ii) ether repeat units, (iii) ester repeat units, (iv) non-sulfonated monocarboxylic repeat units, and (v) amide-containing repeat units, said polymer comprising about 20-55 mole percent repeat units derived from maleic acid and/or anhydride, about 35-65 mole percent repeat units derived from itaconic acid and/or anhydride, and about 2-40 mole percent repeat units derived from sulfonated monomers, where the total amount of all of the repeat units in the polymer is taken as 100 mole percent.

7. The polymer of claim 6, said polymer comprising about 25-50 mole percent repeat units derived from maleic acid and/or anhydride, about 40-60 mole percent repeat units derived from itaconic acid and/or anhydride, and about 3-25 mole percent repeat units derived from sulfonated monomers, where the total amount of all of the repeat units in the polymer is taken as 100 mole percent.

8. The polymer of claim 6, said polymer comprising about 30-45 mole percent repeat units derived from maleic acid and/or anhydride, about 40-55 mole percent repeat units derived from itaconic acid and/or anhydride, and about 5-20 mole percent repeat units derived from sulfonated monomers, where the total amount of all of the repeat units in the polymer is taken as 100 mole percent.

* * * * *